United States Patent
Tempesta et al.

(10) Patent No.: US 11,246,846 B2
(45) Date of Patent: Feb. 15, 2022

(54) TRISODIUM CITRATE COMPOSITIONS HAVING ENHANCED UPTAKE ACROSS DIGESTIVE MUCOSA

(71) Applicants: Michael S. Tempesta, El Granada, CA (US); F. Joseph Daugherty, Omaha, NE (US)

(72) Inventors: Michael S. Tempesta, El Granada, CA (US); F. Joseph Daugherty, Omaha, NE (US)

( * ) Notice: Subject to any disclaimer, the term of this patent is extended or adjusted under 35 U.S.C. 154(b) by 0 days.

(21) Appl. No.: 16/167,323

(22) Filed: Oct. 22, 2018

(65) Prior Publication Data

US 2020/0397729 A1     Dec. 24, 2020

Related U.S. Application Data

(60) Provisional application No. 62/576,007, filed on Oct. 23, 2017.

(51) Int. Cl.

| | |
|---|---|
| *A61K 31/194* | (2006.01) |
| *A61K 31/198* | (2006.01) |
| *A61K 9/00* | (2006.01) |
| *A23L 33/175* | (2016.01) |
| *A23L 29/00* | (2016.01) |
| *A61K 47/10* | (2017.01) |
| *A61K 47/32* | (2006.01) |
| *A61K 47/40* | (2006.01) |
| *A23L 33/18* | (2016.01) |
| *A61K 45/06* | (2006.01) |

(52) U.S. Cl.
CPC .......... *A61K 31/194* (2013.01); *A23L 29/035* (2016.08); *A23L 33/175* (2016.08); *A23L 33/18* (2016.08); *A61K 9/0053* (2013.01); *A61K 31/198* (2013.01); *A61K 47/10* (2013.01); *A61K 47/32* (2013.01); *A61K 47/40* (2013.01); *A61K 45/06* (2013.01)

(58) Field of Classification Search
CPC .. A61K 31/194; A61K 31/198; A61K 9/0053; A61K 47/10; A61K 47/32; A61K 47/40; A61K 45/06; A23L 33/175; A23L 29/035; A23L 33/18
See application file for complete search history.

(56) References Cited

U.S. PATENT DOCUMENTS

| | | | |
|---|---|---|---|
| 5,767,159 A | 6/1998 | Hultman et al. | |
| 5,908,864 A | 6/1999 | Casey | |
| 5,968,000 A | 10/1999 | Harrison et al. | |
| 5,968,544 A | 10/1999 | Howard et al. | |
| 6,136,339 A | 10/2000 | Gardiner | |
| 6,326,513 B1 | 12/2001 | An et al. | |
| 6,620,425 B1 | 9/2003 | Gardiner | |
| 6,784,209 B1 | 8/2004 | Gardiner et al. | |
| 2005/0276847 A1* | 12/2005 | Roberts | A61K 9/2077 424/464 |
| 2006/0062849 A1* | 3/2006 | Byrd | A61K 2300/00 424/468 |
| 2017/0142993 A1 | 5/2017 | Neiss | |

OTHER PUBLICATIONS

Cooper et al. (J. Int. Sports Nutrition; (2012); 9:33).*
Ogawa et al. (The American Physiological Society 1603-1607).*
Cooper, et al., Creatine Supplementation with Specific View to Exercise/Sports Performance: An Update, Journal of the International Society of Sports Nutrition 2012, 9:33.
Product literature for Cell-Tech by Muscle Tech Company, https://www.muscletech.com/products/cell-tech/.
Product label for Cell-Tech by Muscle Tech Company, https://shop.muscletech.com/products/cell-tech.
Hoshino et al., Sodium-Dependent Transport of L-Leucine in Membrane Vesicles Prepared from Pseudomonas Aeruginosa, Journal of Bacteriology, Jan. 1979, pp. 73-81.
Hoshino, Transport Systems for Branched-Chain Amino Acids in Pseudomonas Aeruginosa, Journal of Bacteriology, Sep. 1979, pp. 705-712.
Dash et al., Solid-State Properties of Creatine Monohydrate, Journal of Pharm. Sciences, vol. 91, No. 3, Mar. 2002, pp. 708-717.
Dash, et al., Evaluation of Creatine Transport Using Caco-2 Monolayers as an In Vitro Model for Intestinal Absorption, Journal of Pharm. Sciences, vol. 90, No. 10, Oct. 2001, pp. 1593-1598.

* cited by examiner

*Primary Examiner* — Shirley V Gembeh

(74) *Attorney, Agent, or Firm* — Luke C. Holst; McGrath North Mullin & Kratz, PC LLO

(57) ABSTRACT

The present invention relates to formulations of certain amino acids, peptides and similar molecules in combination with trisodium citrate exhibiting improved bioavailability and enhanced uptake across digestive mucosa. The present invention relates particularly to formulation of trisodium citrate in combinations with leucine, iso-leucine, valine, arginine, sarcosine, glutathione, carnosine, glucosamine, creatine, protein hydrolysates and/or gamma-aminobutyric acid exhibiting improved uptake across digestive mucosa. More particularly, the improved uptake across digestive mucosa takes place across intestinal, esophageal and/or stomach mucosa.

36 Claims, 10 Drawing Sheets

Total Leucine Diffusion Across Caco2 Monolayer

Total Creatine Permeation through Caco2 Monolayer

Total Leucine Permeation through Caco2 Monolayer

Total L-Arginine Permeation through Caco2 Monolayer

Total Citrulline Permeation through Caco2 Monolayer

Total Leucine Permeation through Caco2 Monolayer

Total L-Arginine Permeation through Caco2 Monolayer

Total L-Citrulline Permeation through Caco2 Monolayer

Total L-Leucine Permeation through Caco2 Monolayer

Total Sarcosine Permeation through Caco2 Monolayer

Total L-Leucine Permeation through Caco2 Monolayer

Total Leucine Permeation through Caco2 Monolayer

Total Leucine Permeation through Caco2 Monolayer

Total GABA Permeation through Caco2 Monolayer

Total Leucine Permeation through Caco2 Monolayer

Total IsoLeucine Permeation through Caco2 Monolayer

Total Valine Permeation through Caco2 Monolayer

Total Creatine Permeation through Caco2 Monolayer

Total Leucine Permeation through Caco2 Monolayer

TRISODIUM CITRATE COMPOSITIONS HAVING ENHANCED UPTAKE ACROSS DIGESTIVE MUCOSA

PRIOR APPLICATION

The present application claims priority of U.S. Provisional Application No. 62/576,007 filed Oct. 23, 2017 and entitled Leucine and Sodium Citrate Compositions Having Enhanced Uptake Across Digestive Mucosa, which is incorporated herein in its entirety by this reference.

FIELD OF THE INVENTION

The present invention relates to formulations of trisodium citrate together with leucine, iso-leucine, valine, arginine, sarcosine, glutathione, and gamma-aminobutryric acid, having improved bioavailability across digestive mucosa.

BACKGROUND OF THE INVENTION

Leucine is an α-amino acid, which is an essential branched-chain amino acid used in the biosynthesis of proteins. It contains an α-amino group, an α-carboxylic acid group, and an isobutyl side chain, and functions as a nonpolar amino acid at physiological pH. It is used in the liver, adipose tissue and muscle tissue and is essential in humans—meaning the body cannot synthesize it and thus must obtain it from the diet. Leucine is one of the few amino acids that is completely oxidized in the muscle for energy, and is the only amino acid whose catabolism generates HMGCoA, an intermediate in cholesterol synthesis. Leucine is available in foods such as brown rice, beans, meats, nuts, soy and whole wheat products. It has been shown to stimulate protein synthesis when taken regularly while on a strength training regimen, without any significant side effects. Iso-leucine and valine are other branched-chain amino acids which are of interest as dietary supplements.

Amino acids, including leucine compete for absorption into intestinal cells. There are a limited number of leucine carriers into the intestinal cell, suggesting there is a maximum effective dose. Enhancing the uptake of leucine may therefore aid in maximizing its benefits by increasing availability.

Transport of leucine has been studied in efforts to improve uptake and bioavailability of leucine and other branched-chain amino acids in prokaryotic cells. An article by T. Hoshino et al., entitled "Sodium-Dependent Transport of L-Leucine in Membrane Vesicles prepared from *Pseudomonas aeruginosa*", *Journ. of Bact.*, January 1979, pp 73-81, concludes that "a common transport system for branched-chain amino acids exists in membrane vesicles . . . [and] that the system requires Na+ for its activity . . . ". More particularly, the article concludes that "leucine transport was found to be specifically dependent on Na+[and that t]he addition of other monovalent cations such as K+, Rb+, Cs+, NH4+ and choline had little effect on leucine update . . . . "Li+ alone substituted partially for Na+". Id at 75. Sodium in the form of NaCl, NaNo$_3$ and Na$_2$SO$_4$ was tested. Further research by T. Hoshino reported in "Transport Systems for Branched-Chain Amino Acids in *Pseudomonas aeruginosa*", *Journ. of Bact.*, September 199, pp 705-12, expanded the applicability of the Na transport dependent system beyond leucine to iso-leucine and to valine. It should be noted that the leucine transport system for the prokaryotic cells used in these Hoshino tests may not be identical to the leucine transport systems utilized by eukaryotic cells, or mammalian cells, such as those that make up the mammalian alimentary tract mucosa.

Thus, it is known that in vivo, the sodium from sodium chloride is critical to our ability to absorb amino acids—the building blocks of carbohydrates and proteins, respectively—from the small intestine into the bloodstream. More particularly, when proteins are consumed, they are digested into their building blocks and intestinal cells then move them into the bloodstream. This process requires the presence of sodium, since sodium activates the transporter proteins that shuttle the building blocks across the intestinal lining. The luminal plasma membrane of the absorptive cell bears sodium-dependent amino acid transporters—for acidic, basic, neutral amino acids. These transporters bind amino acids only after binding sodium, also referred to as receptor dependent sodium channel absorption. The fully loaded transporter then undergoes a conformational change that releases sodium and the amino acid into the cytoplasm, followed by reorientation back to its original form. The basolateral membrane of the enterocyte contains additional transporters which export amino acids from the cell into blood. These additional transporters are not dependent on sodium gradients.

In contrast to the branched-chain amino acid leucine, creatine is a substance the body naturally produces in the liver, pancreas and kidneys. Typically, 1 to 2 grams per day of creatine are produced and excreted, and most people consume 1 to 2 grams of creatine per day from food. Creatine is preferentially taken up by skeletal muscle and is composed of three amino acids: methionine, arginine and glycine. Creatine is widely used as a dietary supplement for performance enhancement by athletes because once the creatine is present muscle tissue where it is stored as creatine phosphate, it reacts with adenosine diphosphate (ADP) to restore ADP levels and provide energy for muscle activity. By ingesting creatine, athletes are able to load their muscle tissue with higher levels of creatine phosphate and are able to better sustain muscle activity.

Although many forms of creatine are stable ex vivo, including creatine monohydrate and numerous esters, creatine and creatine monohydrate are known to be typically unstable in vivo, i.e., in the acidic environment that exists in the stomach, and the basic conditions of the lower gastro-intestinal tract. So, for example, it is known that creatine monohydrate, which is a commonly ingested form of creatine, if not taken up promptly, can rapidly break down in the stomach to form creatinine. Furthermore, because creatine monohydrate is not fully solubilized easily in cold or room temperature water, it is often dissolved in fruit juices and other acidic liquids, which also promote degradation of creatine to creatinine and excretion. For these reasons, other forms of creatine, particularly creatine ethyl esters, have been the focus of product development. However, such compounds also suffer from solubility and degradation problems. Properties of creatine monohydrate ($C_4H_{11}N_3O_3$) are described in more detail in A. K. Dash, et al., "Solid State Properties of Creatine Monohydrate", *Journ. of Pharm. Sciences*, Vol. 91, No. 3, March 2002, pp. 708-17.

Even if a particular form of creatine is protected from degradation prior to desired point of uptake in the digestive tract, once the particular form of creatine arrives at the place in the digestive where uptake is desired, transport across the particular mucosal cells is not fully understood and often suboptimal. To more easily test cell transport using a model which meaningfully approximates in vivo digestive tract absorption, researchers now utilize the Caco-2 eukaryotic (mammalian) cell line, a continuous cell of heterogeneous epithelial adenocarcinoma cells developed by the Sloan-Kettering Institute for Cancer Research which resembles enterocytes lining the small intestine. Utilization of the Caco-2 cell line to measure creatine transport has been described by researchers at Creighton University and the University of Nebraska Medical Center in the following publication: A. K. Dash, et al., "Evaluation of Creatine Transport Using Caco-2 Monolayers as an In Vitro Model for Intestinal Absorption", *Journ. of Pharm. Sciences*, Vol. 90, No. 10, Oct. 10, 2001, pp. 1593-98. The article describes how the researchers examined creatine transport using confluent monolayers Caco-2 for their permeability studies. It was concluded that permeability of creatine via Caco-2 monolayers was quite low and bidirectional in nature. It was also found that utilization of an effervescent formulation of creatine did not enhance membrane transport properties. So, although superior technique of enhanced uptake of creatine did not result from this research project, a viable in vivo method of testing creatine transport across mammalian mucosal cells was described.

Relevant to both the continuing need for an improved creatine supplement and an improved leucine supplement, a product in powder form has been described under the product name Cell-Tech by the MuscleTech Company. According to one such product label, one scoop of the Cell-Tech supplement contains 15 g sugar, 125 mg ascorbic acid, 5 mg vitamin B6 (pyridoxine hydrochloride), 45 mg calcium, 33 mg magnesium (magnesium oxide), 35 mg sodium, 25 mg potassium (di-potassium phosphate), 4 g creatine monohydrate, 2 g creatine HCl, 1 g taurine, 500 mg L-alanine, 500 mg L-leucine, 250 mg L-valine, 250 mg L-isoleucine and 100 mg lipoic acid. Other product literature describes the sodium source as NaCl. Of particular interest to the inventors of the present invention are the weight ratios of sodium to the two forms of creatine and to the branched-chain amino acids. Basing calculations of molar weights for these constituents as 23 g/mol for sodium, 149.15 g/mol for creatine monohydrate, 167.593 g/mol for creatine HCl, 131.18 g/mol for leucine and iso-leucine and 117.15 g/mol for valine, the molar equivalent ratios for total creatines: branched-chain amino acids:sodium are believed to be (when rounded to nearest integer) 26:5:1. Put another way, in this MuscleTech formulation, the ratio by weight of sodium to the total weight of creatine monohydrate+creatine HCl+leucine+valine+iso-leucine=0.035:7.0=0.5% by weight of sodium.

Other product literature for MuscleTech describes another formulation as containing 7 g of creatine monohydrate and 3 g of creatine HCl per serving. Product literature for Cell-Tech also presently describes the product as protected by multiple patents, including U.S. Pat. Nos. 5,968,000, 6,136,339, 6,620,425, 5,767,159, 5,968,544 and 6,326,513.

Nonetheless, it is believed that a significantly improved formulation of creatine by itself or together with one or more branched-chain amino acids is needed to substantially improve bioavailability and uptake without including minimally helpful and unnecessary constituents (such as, for example, sugar) in order to advance the pharmacokinetics and pharmacodynamics aspects of the formulations. Such technical improvements should also allow a set of new uses to possibly address more effectively disorders such as cachexia and Sarcopenia in addition to traditional muscle building and maintenance applications to which creatine and/or leucine supplementation have been historically directed.

SUMMARY OF THE INVENTION

The present invention relates to formulations of leucine, iso-leucine, valine, arginine, sarcosine, glutathione, carnosine, glucosamine, gamma-aminobutryric acid, and creatine having improved bioavailability. More particularly, the present invention relates particularly to formulations of leucine, iso-leucine, valine, arginine, sarcosine, glutathione, carnosine, glucosamine, protein lysates, gamma-aminobutryric acid and/or creatine in combination with trisodium citrate exhibiting improved uptake across digestive mucosa, including intestinal, esophageal, and stomach mucosa.

As used herein, trisodium citrate ("TSC") has a molecular formula of $Na_3C_6H_5O_7$ and is also known as trisodium 2-hydroxypropane-1,2,3-tricarboxylate. The anhydrous form has a molecular weight of 258.06 g/mol and the dihydrate form has a molecular weight of 294.10 g/mol, both forms being encompassed by the TSC abbreviation.

Embodiments of the present invention increasing the uptake or bioavailability of certain nonessential amino acids, alone or in combination with leucine, include but are not limited to alanine (from pyruvic acid), arginine (from glutamic acid), asparagine (from aspartic acid), aspartic acid (from oxaloacetic acid), cysteine, glutamic acid (from oxoglutaric acid), glutamine (from glutamic acid), glycine (from serine and threonine), proline (from glutamic acid), serine (from glucose) and tyrosine (from phenylanine) all of which may be enhanced by combining with TSC. Uptake of certain essential amino acids may be similarly enhanced by combining with leucine and trisodium citrate).

In one aspect of the present invention, compositions are produced with mixtures of dry ingredients, preferably powders, or by co-granulation of active materials with or without excipients. The compositions may preferably be produced by mixing dry compositions of TSC, with powdered leucine (with or without other amino acids, protein lysates, peptides and proteins) for subsequent ingestion. Alternatively, powdered leucine, alone or in combination with valine and/or iso-leucine, may be mixed with trisodium citrate, and optionally combined with creatine, most preferably creatine monohydrate, for a combination having improved transport across mucosal cells. Preferably, the active ingredients are mixed or co-granulated to an average size of 150 to 840μ (microns) in size, more preferably to an average size of 250-500μ, and most preferably to an average size of 350-450μ. The size and co-granulation time are sized and selected to result in particles within a specific range and to allow for raw material uniformity. US Mesh screens of 20-300 are preferably used to ensure that the particles are suitable for subsequent tableting or used as powders, as desired. The preferred particle size may be selected with an eye to interlocking particular active ingredient(s) with other constituents.

In one most preferred form of the supplement produced with this method, the active ingredients include creatine monohydrate, leucine and TSC.

A most preferred formulation includes leucine and/or other branched-chain amino acid with TSC, as such a formulation provides a substantial and sufficient quantity of sodium in such a form that optimizes transport and absorption of the one or more branched-chain amino acid(s) and a synergistic relationship is believed to result, thereby enhancing the transport of the amino acid(s) to an extent not seen when other salts alone (such as when sodium chloride and/or sodium ascorbate are used). Most preferable formulations of leucine (and/or other branched-chain amino acid) to TSC results when the weight percent of the sodium in the TSC to the leucine (or to the total of all branched-chain amino acids) is preferably at least 2% by weight, although if the dosage of branched-chain amino acid(s) and optionally creatine monohydrate constitutes at least 5 g, then the weight percent of the sodium in TSC is accepted to produce an enhanced effect if it constitutes at least 1% of the branched chain amino-acids/creatine monohydrate combination. Other acceptable dosage ranges by weight of the sodium in the TSC to the one or more branched-chain amino acids (and optional creatine monohydrate) are when the one or more branched-chain amino acids constitute from 5-20 g and the sodium from the TSC constitutes 1-19% by weight, (or even 0.5% by weight if the dosage of branched-chain amino acids and optional creatine is from 10-20 g), more preferably 2-15% by weight, even more preferably 2-10% by weight, and most preferably 3-10% by weight.

When creatine by itself or is included in the compositions of the present invention, especially if the preferred form of creatine—creatine monohydrate—is included in the formulations of the present invention along with trisodium citrate ("TSC"), the most preferred molar ratio of creatine monohydrate:leucine:sodium wherein the sodium source is trisodium citrate, is 2:2:0.25. It is expected that an enhanced transport effect will be present when the molar ratio of creatine monohydrate:leucine:sodium is from 1:1:0.25 to 1:1:3, or when percentages by weight of sodium are from approximately 2% to 19%. However, the more creatine and leucine (and/or other branched-chain amino acids present in a dose, less sodium from TSC is expected to exhibit an enhanced bioavailability. So for example, if 10 g of leucine (and/or other branched-chain amino acids) and 10 g of creatine monohydrate, 1.5 g of TSC gives an acceptable amount of sodium of approximately 1.8% sodium from the TSC.

Preferred daily dosing range of leucine (and/or other branched-chain amino acids) is from 1 to 10 grams, of TSC is from 500 mg to 5 grams, and, optionally, creatine monohydrate is from 1 to 10 grams. More preferred dosages of leucine and TSC are 1.0-5 grams and 0.5 to 2.5 grams, respectively. Most preferred dosages of leucine and TSC are 3 grams and 1.5 grams, respectively. If creatine monohydrate is also included in the composition to be ingested than an additional 1.0-5 grams of creatine monohydrate is preferred. Most preferred is a dosage that includes 3 grams of leucine, 3 grams of creatine monohydrate and 1.5 grams of TSC for a weight ratio of 2:2:1 of the 3 components (leucine:creatine monohydrate:TSC, respectively).

In terms of molar equivalents, most preferable dose formulations of leucine (and/or other branched-chain amino acid) to TSC are when the moles of leucine (or the total moles of all branched-chain amino acids) range from 0.0076 (7.6 millimoles (mM)) to 0.076 (76 mM) moles and the moles of TSC range from 0.0019 (1.9 mM) to 0.019 (19 mM) moles. If, at one end of this spectrum, a dose comprises 0.0076 moles (7.6 mM) of leucine and/or other branched chain amino acids and 0.0019 moles (1.9 mM) of TSC, the molar ratios may be reduced to 4:1. Since each mole of TSC comprises 3 moles of sodium, it can be seen that the most preferred ratio of the present invention of leucine and/or other branched-chain amino acids to sodium from TSC is 4:3. At the other end of the spectrum, if 0.076 moles (76 mM) of leucine and/or other branched chain amino acid are mixed with only 0.0019 moles (1.9 mM) of TSC, then it the molar ratio of the mixture if 0.004 to 0.0001 which can also be described as 40:1. Since there are 3 moles of sodium for each 1 mole of TSC, then the lower limit of an acceptable molar ratio of leucine and/or other branched-chain amino acid to sodium from TSC is 40:3.

Preferred daily dosing ranges of leucine (and/or other branched-chain amino acids) is from 1 to 10 grams, of TSC is from 400 mg to 5 grams, and, optionally, creatine monohydrate is from 1 to 10 grams. More preferred dosages of leucine and TSC are 1.5-4.5 grams and 0.75 to 2.5 grams, respectively. Preferred daily dosage ranges of creatine monohydrate by itself is from 1 to 10 grams and of TSC. Most preferred dosages of leucine and TSC re 3 grams and 1.5 grams, respectively. If creatine monohydrate is also included in the composition to be ingested than an additional 1.5-4.5 grams of creatine monohydrate is preferred. Preferred daily dosing ranges of creatine monohydrate by itself is from 1 to 10 grams and of TSC is from 400 mg to 5 grams. In alternate embodiments, the creatine monohydrate may be substituted in part or all with creatine hydrochloride, creatine ethyl ester, creatine hydrochloride, creatine phosphate, creatine pyruvate, creatine ascorbate, creatine gluconate, creatine citrate, creatine nitrate, creatine magnesium chelate, and/or the salt forms of these listed creatines, provided that the uptake enhancements exhibited when creatine monohydrate is employed in combination with TSC are present.

Also, while leucine is the most preferred branched-chain amino acid for use in the formulations of the present invention, one or more branched-chain amino acids selected from the group consisting of leucine, valine and isoleucine may be substituted in all or part for the leucine component of the present invention.

It is further contemplated that the creatine formulations of the present invention may be useful for minimizing symptoms of Parkinson's disease and of muscle-wasting diseases. Higher dosages, for example, from 2 to 20 grams per day, are recommended to minimize symptoms of Parkinson's disease and muscle wasting diseases and conditions. Higher dosages may also be tolerated and useful for body builders and others involved in frequent, high energy demand sports, such as, for example, individuals weight lifting, power lifting, crossfit, mountain biking, road cycling, or similarly demanding sport, 2 or more hours a day, 3 or more days a week.

DETAILED DESCRIPTION OF PREFERRED EMBODIMENTS

Initially, in order to make a meaningful evaluation of sodium transport of branched-chain amino acids across eukaryotic mucosal cells of the human digestive tract, the inventors elected to test leucine transport using the Caco-2 monolayer model similar to that described by Dash, et al. in "Evaluation of Creatine Transport Using Caco-2 Monolayers" id. The tests were undertaken using a Caco-2 cells so as to more closely approximate transport of creatine and branched-chain amino acids across mucosal cell membranes in vivo than might be reflected in other utilizing non-human cell sources or non-mucosa cell sources. In the permeation tests illustrated herein, simulated gastric and intestinal buffers were made with 0.2 normal (N) NaOH, made by mixing 1 g NaOH as needed with 125 mL deionized water. To simulate intestinal fluid without enzymes, 6.8 g monobasic potassium phosphate were mixed in 77 mL 0.2 N sodium hydroxide, and pH adjusted to 6.8±0.1 using NaOH or HCl, as needed. Thereafter, the solution was diluted to 1 L with deionized water, with a final pH of about 6.8±0.1. To simulate gastric fluid without enzymes, 2.0 g sodium chloride was added to 7.0 mL concentrated HCl, and then diluted to 1 L with deionized water. The pH was approximately 1.2

Example I

Figure 1:
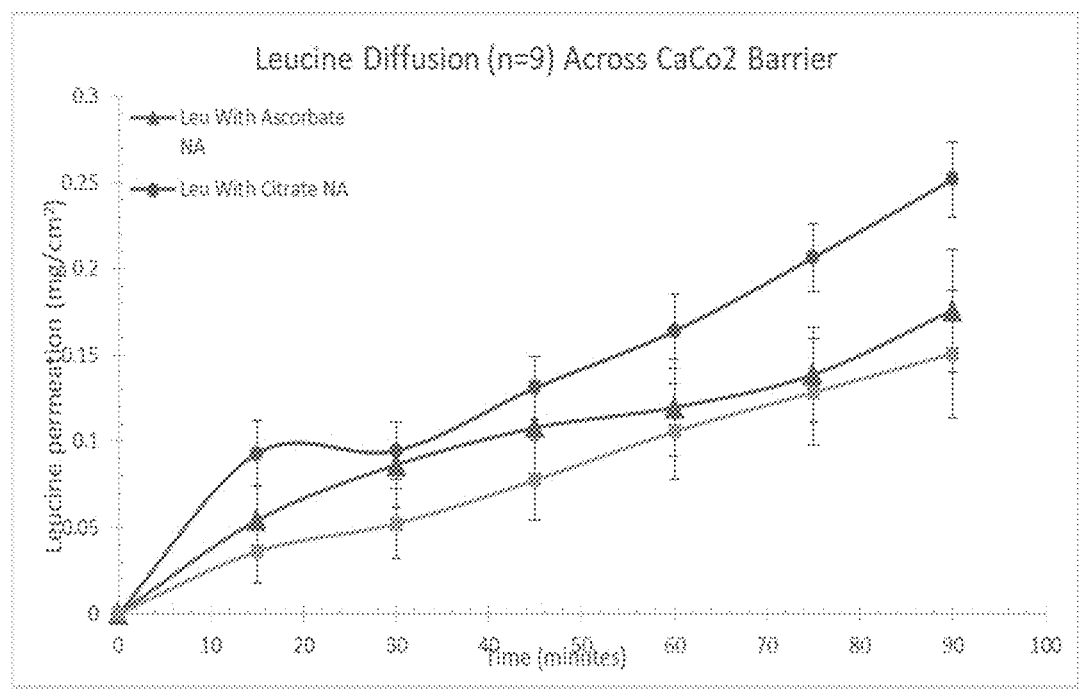
FIG. 1 is a graph comparing leucine diffusion across a Caco2 barrier from solutions of (1) leucine, (2) leucine+sodium ascorbate, and (3) leucine+trisodium citrate ("TSC"), wherein milligrams (mg) of leucine permeation per centimeter squared ($cm^2$) is plotted for samples taken at 15 minute intervals over a 90 minute test.

The inventors elected to initially test leucine transport across mucosal cells alone as compared to leucine with sodium ascorbate and leucine with trisodium citrate ("TSC"). A repetition in a series of three repetitions was then undertaken to examined the changes in permeation in the presence of a different form of sodium as compared to leucine alone in Hank's Balanced salt solution across a Caco-2 model intestinal barrier (TEER≥1000 ohm*cm2). FIG. 1 represents the data from all 3 studies for leucine alone, leucine+sodium ascorbate, and leucine+TSC. Leucine permeation across the Caco-2 monolayer was measured at 15, 30, 45, 60, 75 and 90 minutes after test initiation in milligrams of leucine per centimeter2 (mg/cm2). Data is summarized in Table I below and illustrated in FIG. 1.

Most unexpectedly, there was a consistently significant increase in the permeation of leucine in the presence of TSC as compared to the leucine in the presence of sodium ascorbate. All studies showed a slight increase in the permeation of leucine in the presence of sodium ascorbate, however upon final collation of data this was determined to not be significant. None of the studies showed significant damage to the cell layer.

TABLE I

|  | 15 min | 30 min | 45 min | 60 min | 75 min | 90 min | Baseline adj for Leucine w/o Na |
|---|---|---|---|---|---|---|---|
| Leucine | 0.036 | 0.052 | 0.078 | 0.106 | 0.128 | 0.151 | 0.00 |
| Leucine + Na ascorbate | 0.054 | 0.086 | 0.108 | 0.120 | 0.139 | 0.176 | 0.025 |
| Leucine + TSC | 0.093 | 0.095 | 0.131 | 0.164 | 0.206 | 0.252 | 0.101 |

What was most surprising and unpredicted was the significantly increased transport of leucine across the Caco-2 mucosa cells when combined with TSC (compared to transport with sodium ascorbate) which was not accounted for alone by the presence of 3 times the amount of sodium present in the 10 mM TSC solution over the amount of sodium in the 10 mM sodium ascorbate solution.

Example II

Thereafter, a set of formulation diffusion studies were undertaken using a Caco-2 cellular model again similar to that described in the publication by A. K. Dash, et al., "Evaluation of Creatine Transport Using Caco-2 Monolayers as an In Vitro Model for Intestinal Absorption". More particularly, after 21 days of growth in Corning® Transwell 6 well plat, trans-epithelial electrical resistance (TEER) was measured across the Caco2 monolayer using an EVOM II TEER meter with an Endohm 24SNAP measuring chambers. Cells were considered ready for use if the average TEER value reached approximately 900 Ohm*cm2. The Caco2 monolayer was then equilibrated in DPBS at 37° C. for 15 minutes. The apical solution was then removed and replaced with the various solutions to be tested. Basolateral chambers were sampled at 15, 30, 45, 60, 75 and 90 minutes and replaced with fresh DPBS. All samples were filtered at 0.45 μm and examined by HPLC. The HPLC analysis utilized a 250 mm×4.6 mm, 5 μm Thermo Scientific BDS Hypersil base deactivated C18 column. The mobile phase consisted of 0.5 M ammonium sulphate at a flow rate of 1.5 m/min. Sample detection was performed at 206 nm using a photodiode array. For this Example II, four formulations were studied, with chemicals present at 10 mM:

(1) Creatine Monohydrate and Leucine only;
(2) Creatine Monohydrate and Leucine with Trisodium Citrate (TSC);
(3) Creatine Monohydrate and Leucine with Sodium Chloride (NaCl); and
(4) Creatine Monohydrate and Leucine with Calcium Citrate (CaCitrate).

Figure 2:
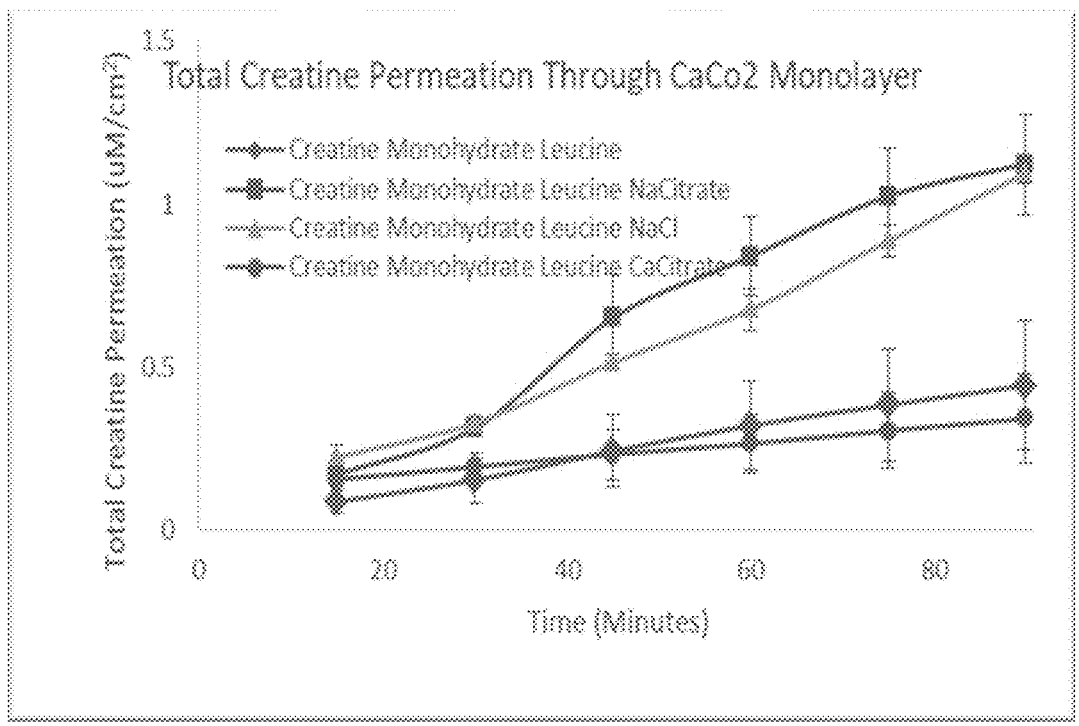
FIG. 2 is a graph comparing creatine diffusion across a Caco2 barrier from solutions of (1) leucine+creatine monohydrate, (2) leucine+creatine monohydrate+TSC, (3) leucine+creatine monohydrate+sodium chloride, and (4) leucine+creatine monohydrate+calcium citrate, wherein micromoles ($\mu M$)/$cm^2$ are plotted for samples taken at 15 minute intervals over a 90 minute test.
Figure 3:
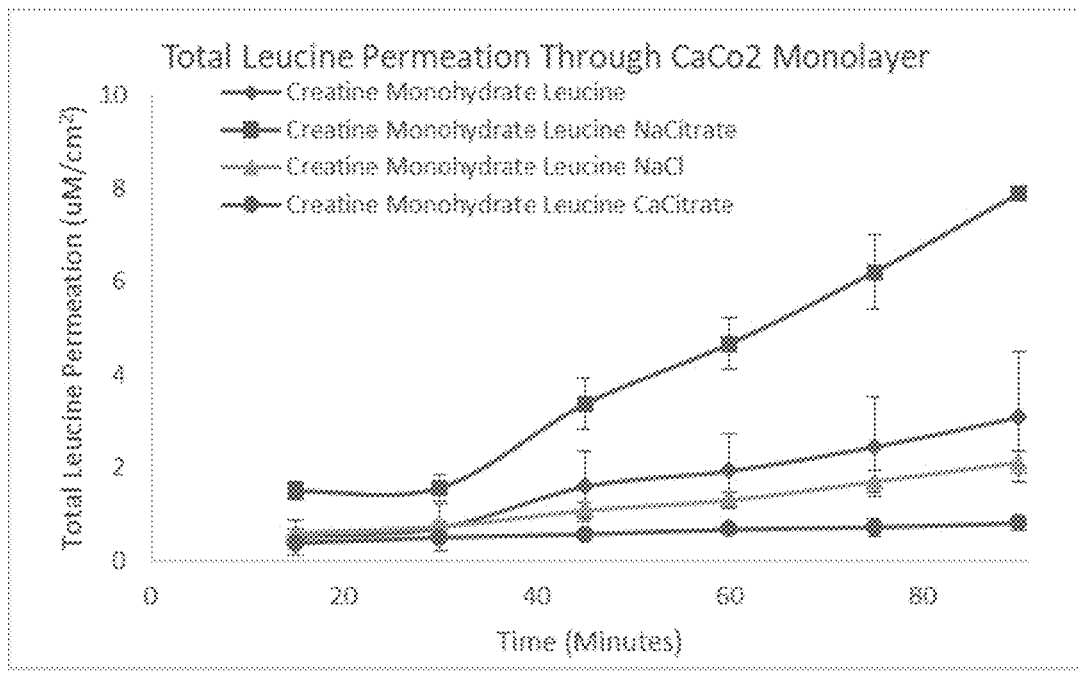
FIG. 3 is a graph comparing leucine diffusion across a Caco2 barrier from solutions of (1) leucine+creatine monohydrate, (2) leucine+creatine monohydrate+TSC, (3) leucine+creatine monohydrate+sodium chloride, and (4) leucine+creatine monohydrate+calcium citrate, wherein $\mu M/cm^2$ are plotted for samples taken at 15 minute intervals over a 90 minute test.

For the experiments in this study samples from each formulation were monitored apical to basolateral through a Caco-2 membrane registering an average TEER of 1650 Ohm*cm². No significant quantities of creatinine were detected during the study. Data shown graphically in FIGS. 2 and 3 is summarized in Table II:

TABLE II

|  | 15 min | 30 min | 45 min | 60 min | 75 min | 90 min | ADJ baseline |
|---|---|---|---|---|---|---|---|
| (1) creatine H2O + leucine CREATINE measured: | 0.088 | 0.154 | 0.243 | 0.321 | 0.385 | 0.444 | 0. |
| (2) creatine H2O + leucine + TSC CREATINE measured: | 0.171 | 0.313 | 0.651 | 0.840 | 1.02 | 1.12 | 0.676 |
| (3) creatine H2O + leucine + NaCl CREATINE measured: | 0.224 | 0.329 | 0.514 | 0.677 | 0.888 | 1.09 | .0.646 |
| (4) creatine H2O + sodium ascorbate CREATINE measured: | 0.156 | 0.195 | 0.233 | 0.265 | 0.306 | 0.342 | — |
| (1) creatine H2O + leucine LEUCINE measured: | 0.511 | 0.712 | 1.60 | 1.94 | 2.45 | 3.09 | 0. |
| (2) creatine H2O + leucine + TSC LEUCINE measured: | 1.50 | 1.58 | 3.37 | 4.67 | 6.21 | 7.90 | 4.81 |
| (3) creatine H2O + leucine + NaCl LEUCINE measured: | 0.605 | 0.741 | 1.09 | 1.31 | 1.71 | 2.12 | — |
| (4) creatine H2O + sodium ascorbate LEUCINE measured: | 0.392 | 0.509 | 0.580 | 0.680 | 0.728 | 0.815 | — |

It was noted that both sodium chloride and TSC enhanced the permeability of creatine monohydrate, but calcium citrate did not. Indeed, the calcium citrate resulted in significantly reduced leucine permeability. Although a certain amount of precipitation was observed in the calcium citrate donor chamber concentrations of leucine and creatine were not reduced and this suggests that the reduced permeability of leucine was not a result of the precipitation.

Most significant, the addition of TSC to leucine and creatine resulted in a surprisingly enhanced increase in the permeability of leucine. While sodium chloride did produce an effect on leucine permeability, this known effect could be best characterized as the baseline effect of sodium chloride transport on leucine, and the enhanced effect resulting from the presence of TSC is not sufficiently accounted for by the presence of the multiple sodium atoms provided by each trisodium citrate molecule. These findings were found by the inventors hereof to be both unexpected and significant.

Example III

Thereafter, further diffusion studies were undertaken using a Caco-2 cellular model similar to that described in connection with Example II above. Four formulations were studied, with chemicals present at 10 mM:

(1) L-Arginine alone;
(2) L-Arginine with Trisodium Citrate (TSC);
(3) L-Citrulline; and
(4) L-Citrulline with Trisodium Citrate (TSC).

For these experiments undyed isotonic DPBS was used as the receiver and donor buffer rather than HBSS due to interference with HBSS components in the HPLC. More particularly, 3 mM 10 mM L-Arginine or L-Citrulline in DPBS alone was tested with 10 mM TSC added to the donor chamber of each of 3 side by side diffusion cells with a confluent Caco 2 Monolayer between (TEER~900 Ohm*cm2). Samples were taken at 15 minute intervals for 90 minutes and replaced with fresh isotonic DPBS. Samples were taken from donor chamber at time 0 and at 90 minutes.

Figure 4:
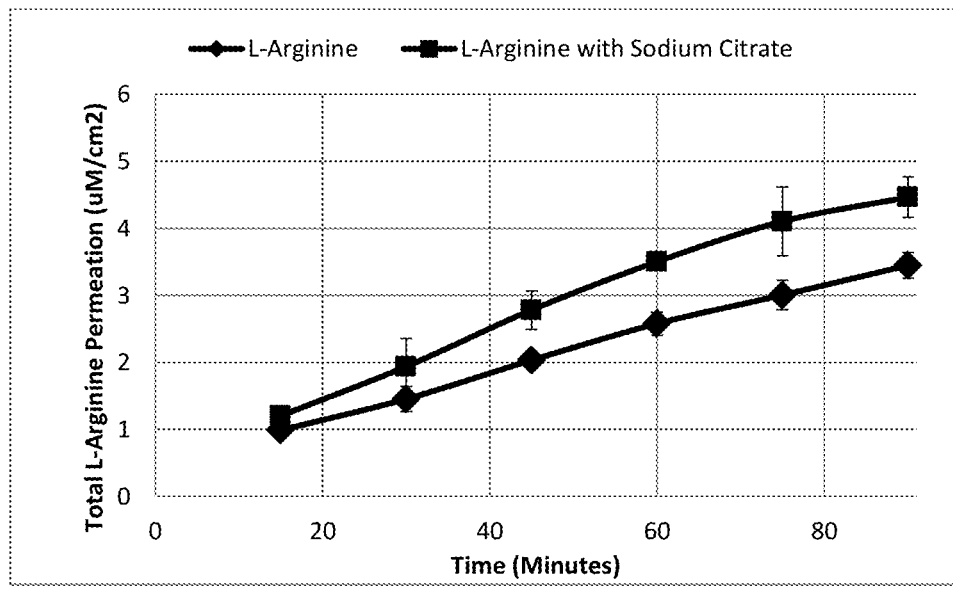
FIG. 4 is a graph comparing arginine diffusion across a Caco2 barrier from solutions of (1) L-arginine, and (2) L-arginine+TSC, wherein $\mu M/cm^2$ are plotted for samples taken at 15 minute intervals over a 90 minute test.
Figure 5:
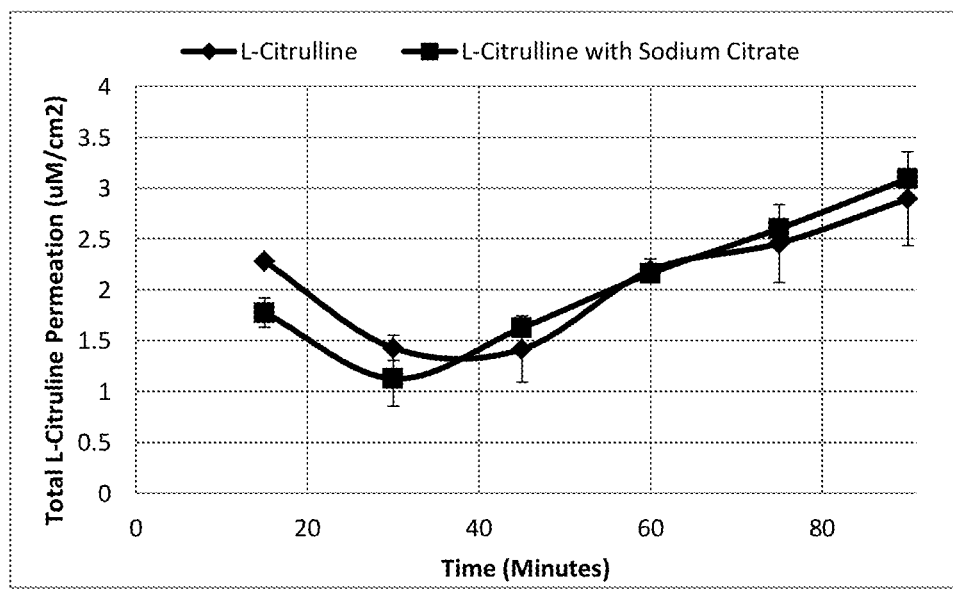
FIG. 5 is a graph comparing citrulline diffusion across a Caco2 barrier from solutions of (1) L-citrulline, and (2) L-citrulline+TSC, wherein $\mu M/cm^2$ are plotted for samples taken at 15 minute intervals over a 90 minute test.

Below are the results of these studies. Data shown graphically in FIGS. 4 and 5 and is summarized in Table III:

TABLE III

|  | 15 min | 30 min | 45 min | 60 min | 75 min | 90 min |
|---|---|---|---|---|---|---|
| (1) L-Arginine alone | 0.988 | 1.453 | 2.033 | 2.578 | 3.005 | 3.448 |
| (2) L-Arginine + TSC | 1.203 | 1.939 | 2.782 | 3.503 | 4.104 | 4.465 |
| (3) L-Citrulline alone | 2.281 | 1.428 | 1.415 | 2.191 | 2.457 | 2.893 |
| (2) L-Citrulline + TSC | 1.775 | 1.126 | 1.624 | 2.161 | 2.601 | 3.092 |

Although L-Citrulline did not show any significant change in permeability in the presence of TSC, L-Arginine showed a significantly greater permeability in the presence of TSC.

Example IV

Figure 6:
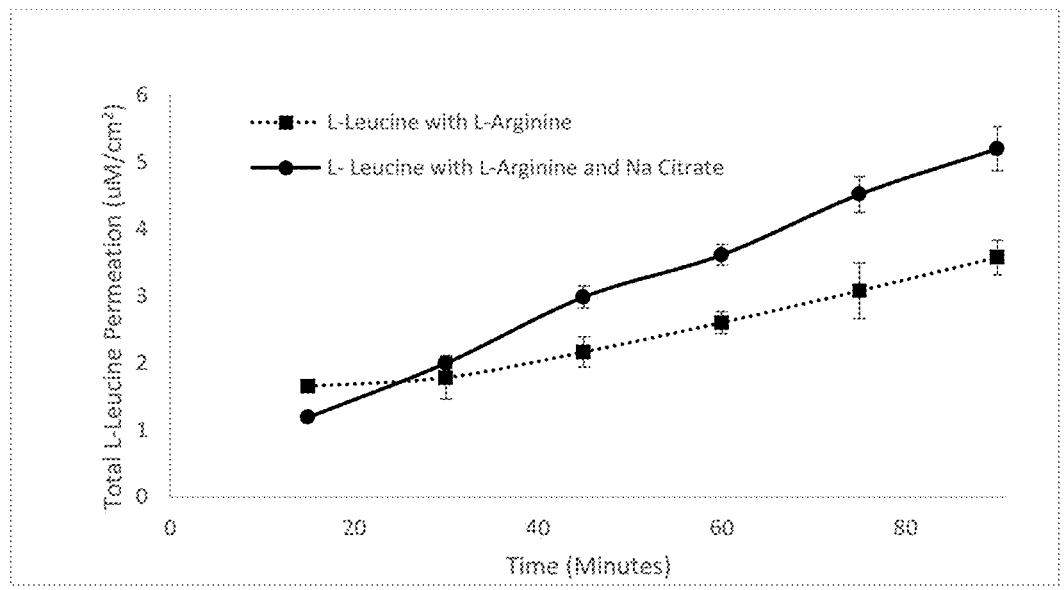
FIG. 6 is a graph comparing leucine diffusion across a Caco2 barrier from solutions of (1) L-leucine+L-arginine, and (2) L-leucine+L-arginine+TSC, wherein $\mu M/cm^2$ are plotted for samples taken at 15 minute intervals over a 90 minute test.
Figure 7:
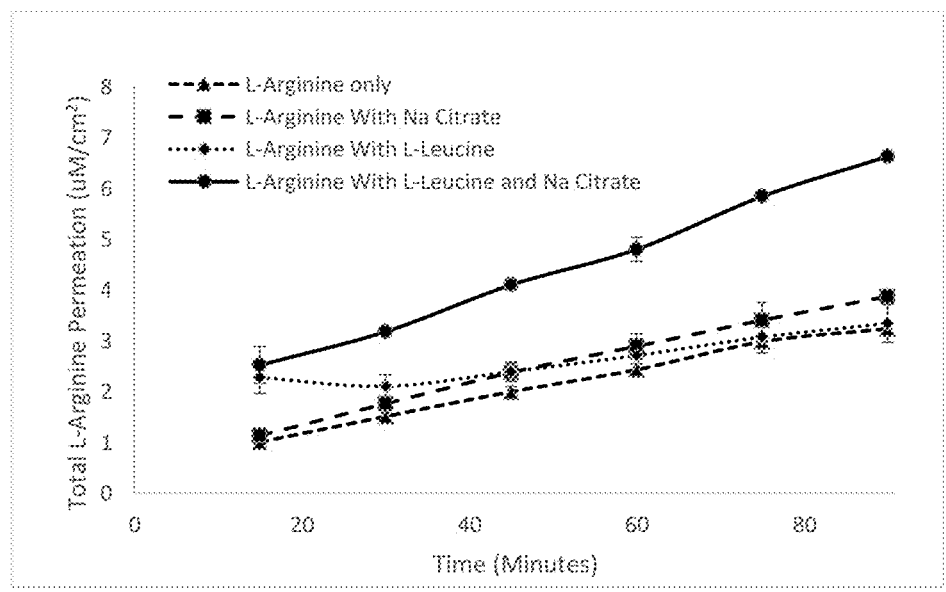
FIG. 7 is a graph comparing arginine diffusion across a Caco2 barrier from solutions of (1) L-arginine, (2) L-arginine+TSC, (3) L-leucine+L-arginine, and (4) L-leucine+L-arginine+TSC, wherein $\mu M/cm^2$ are plotted for samples taken at 15 minute intervals over a 90 minute test.

In further experiments were undertaken using a Caco-2 cellular model similar to that described in connection with Example II above. The permeability of the branched-chain amino acids L-Arginine and L-Leucine through a Caco2 monolayer alone or in combination in the presence and absence of TSC was measured. For these experiments undyed isotonic DPBS was used as receiver and donor buffer rather than HBSS due to interference with HBSS components in the HPLC. Essentially, 3 mL 10 mM L-Arginine or 10 mM L-Arginine and 10 mM L-Leucine in DPBS alone or with 10 mM TSC was added to the donor chamber of each of 3 side by side diffusion cells with a confluent Caco 2 Monolayer between (TEER~900 Ohm*cm2). Samples were taken at 15 minute intervals for 90 minutes and replaced with fresh isotonic DPBS. Samples were taken from donor chamber at time 0 and at 90 minutes. The results of these studies in graphical form are illustrated in FIGS. 6 and 7. The data is summarized in Table IV.

TABLE IV

|  | 15 min | 30 min | 45 min | 60 min | 75 min | 90 min |
|---|---|---|---|---|---|---|
| (1) L-Leucine w/L-Arginine | 1.651 | 1.779 | 2.161 | 2.600 | 3.075 | 3.573 |
| (2) L-Leucine w/L-Arginine + TSC | 1184 | 1.994 | 2.981 | 3.609 | 4.512 | 5.193 |
| (3) L-Arginine alone | 1.007 | 1.511 | 1.999 | 2.432 | 2.982 | 3.237 |
| (2) L-Arginine w/TSC | 1.137 | 1.761 | 2.377 | 2.891 | 3.404 | 3.871 |
| (3) L-Arginine w/L-Leucine | 2.275 | 2.104 | 2.394 | 2.710 | 3.073 | 3.342 |
| (4) L-Arginine w/L-Leucine + TSC | 2.521 | 3.179 | 4.098 | 4.798 | 5.839 | 6.625 |

As previously observed L-Leucine and L-Arginine permeability was enhanced in the presence of trisodium citrate. Although L-Leucine had no effect on L-Arginine permeability by itself, when used with trisodium citrate a significant increase in permeability the L-Arginine was observed.

Example V

Figure 8:
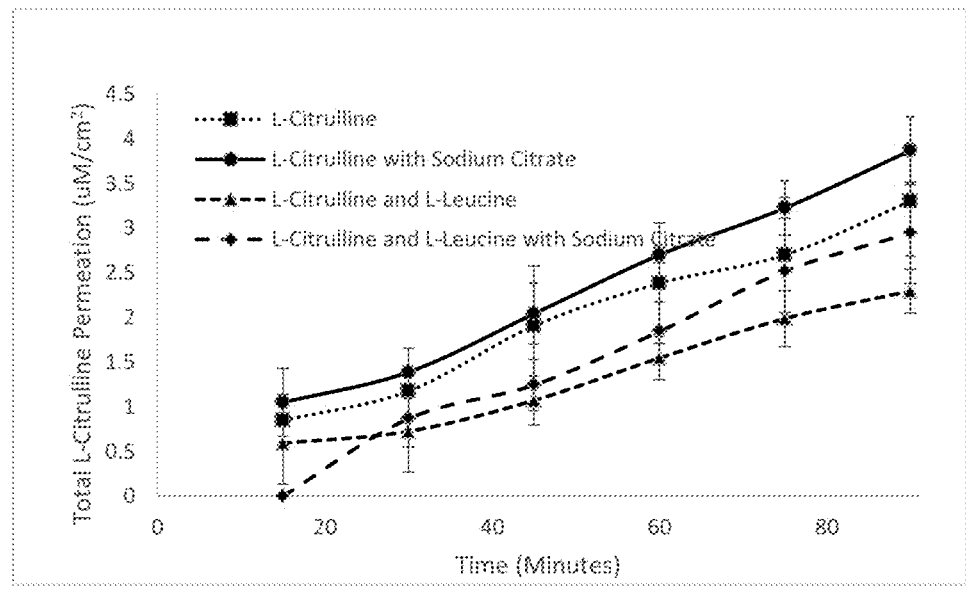
FIG. 8 is a graph comparing citrulline diffusion across a Caco2 barrier from solutions of (1) L-citrulline, (2) L-citrulline+TSC, (3) L-leucine+L-citrulline, and (4) L-leucine+L-citrulline+TSC, wherein $\mu M/cm^2$ are plotted for samples taken at 15 minute intervals over a 90 minute test.
Figure 9:
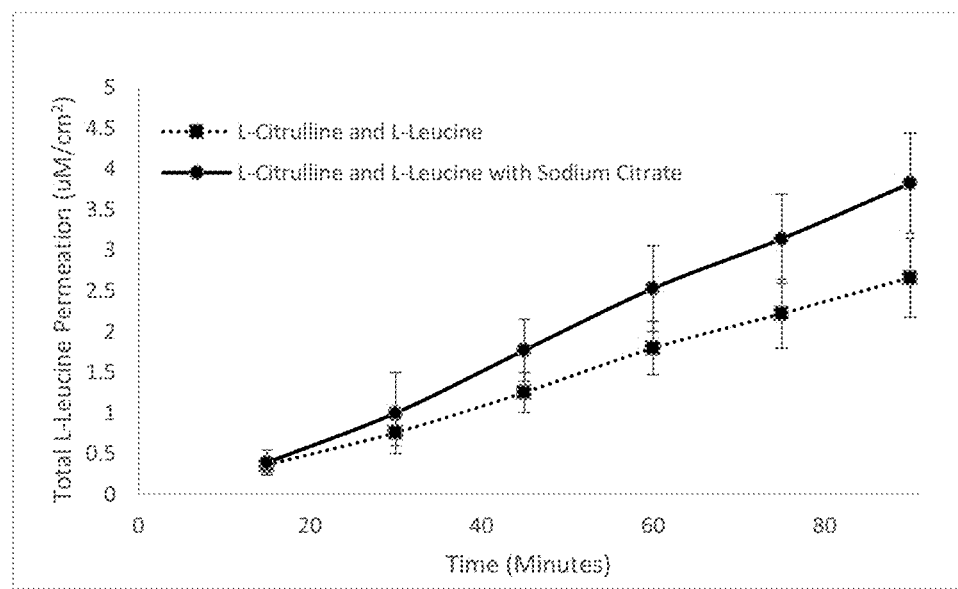
FIG. 9 is a graph comparing leucine diffusion across a Caco2 barrier from solutions of (1) L-leucine+L-citrulline, and (2) L-leucine+L-citrulline+TSC, wherein $\mu M/cm^2$ are plotted for samples taken at 15 minute intervals over a 90 minute test.

Further experiments were then performed test the permeability of the branch chain amino acids L-Citrulline and L-Leucine through a Caco2 monolayer alone or in combination in the presence and absence of TSC. Again, undyed isotonic DPBS was used as receiver and donor buffer rather than HBSS due to interference with HBSS components in the HPLC. In brief 3 mL 10 mM L-Citrulline or 10 mM L-Citrulline and 10 mM L-Leucine in DPBS alone or with 10 mM TSC was added to the donor chamber of each of 3 side by side diffusion cells with a confluent Caco2 Monolayer between (TEER~900 Ohm*cm2). Samples were taken at 15 minute intervals for 90 minutes and replaced with fresh isotonic DPBS. Samples were taken from donor chamber at time 0 and at 90 minutes. The results of the studies in graphical form are illustrated in FIGS. 8 and 9, with data summarized in Table V below.

TABLE V

|  | 15 min | 30 min | 45 min | 60 min | 75 min | 90 min |
|---|---|---|---|---|---|---|
| (1) L-Citrulline alone | 0.846 | 1.174 | 1.906 | 2.381 | 2.699 | 3.300 |
| (2) L-Citrulline + TSC | 1.048 | 1.387 | 2.041 | 2.699 | 3.224 | 3.868 |
| (3) L-Citrulline w/L-Leucine | 0.591 | 0.724 | 1.070 | 1.545 | 1.986 | 2.295 |
| (4) L-Citrulline w/L-Leucine + TSC | — | 0.866 | 1.243 | 1.843 | 2.517 | 2.943 |
| (1) L-Citrulline w/L-Leucine | 0.355 | 0.751 | 1.245 | 1.789 | 2.213 | 2.657 |
| (2) L-Citrulline w/L-Leucine + TSC | 0.384 | 0.992 | 1.737 | 2.522 | 3.133 | 3.812 |

As previously observed L-Leucine permeability was enhanced in the presence of TSC. Also as previously observed there was no significant effect on L-Citrulline permeability by TSC or L-Leucine.

Example VI

Figure 10:
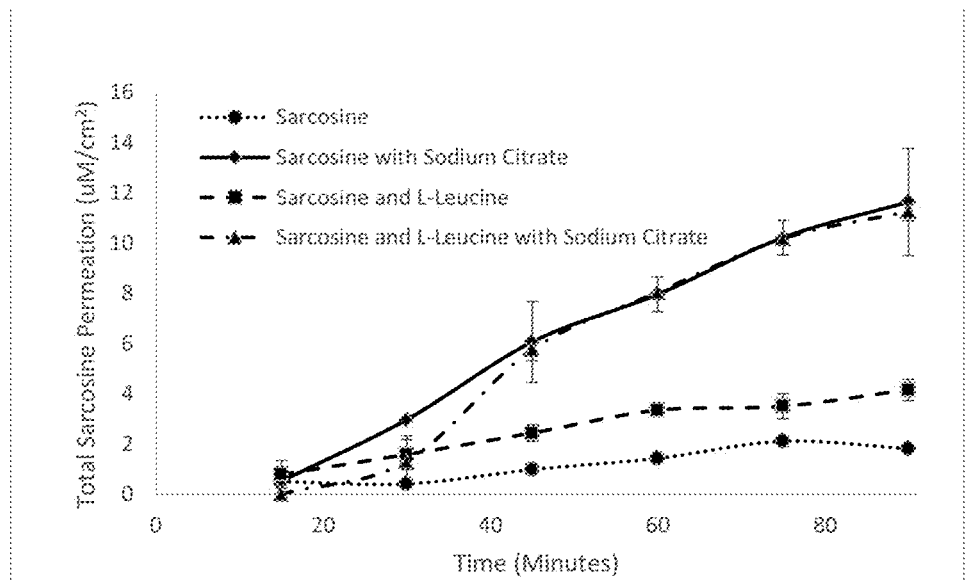
FIG. 10 is a graph comparing sarcosine diffusion across a Caco2 barrier from solutions of (1) L-sarcosine, (2) L-sarcosine+TSC, (3) L-leucine+L-sarcosine, and (4) L-leucine+L-sarcosine+TSC, wherein $\mu M/cm^2$ are plotted for samples taken at 15 minute intervals over a 90 minute test.
Figure 11:
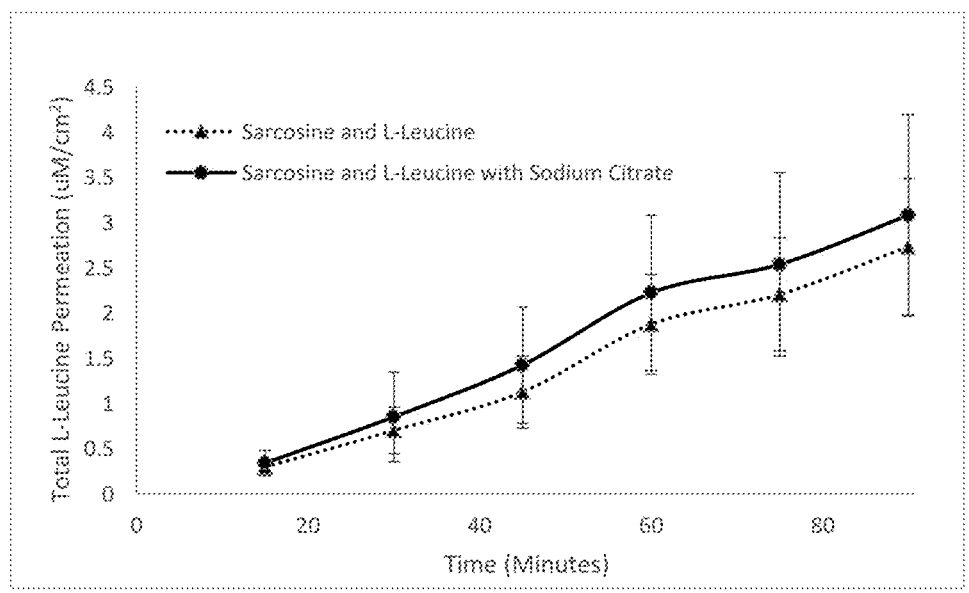
FIG. 11 is a graph comparing leucine diffusion across a Caco2 barrier from solutions of (1) L-leucine+L-sarcosine, and (2) L-leucine+L-sarcosine+TSC, wherein $\mu M/cm^2$ are plotted for samples taken at 15 minute intervals over a 90 minute test.

The permeability of the branch chain amino acids Sarcosine and L-Leucine through a Caco2 monolayer alone or in combination in the presence and absence of TSC were also tested. For these experiments, as before, undyed isotonic DPBS as receiver and donor buffer rather than HBSS due to interference with HBSS components in the HPLC. Procedurally, 3 mL 10 mM Sarcosine or 10 mM Sarcosine and 10 mM L-Leucine in DPBS alone or with 10 mM TSC was added to the donor chamber of each of 3 side by side diffusion cells with a confluent Caco2 Monolayer between (TEER~900 Ohm*cm2). Samples were taken at 15 minute intervals for 90 minutes and replaced with fresh isotonic DPBS. Samples were taken from donor chamber at time 0 and at 90 minutes. On analysis it was discovered that a peak in the receiver side samples which had not interfered with previous samples eluted at the same time as the Sarcosine. The results were adjusted by averaging this peak from time points in previous studies and accordingly, the results represent an estimation by subtraction. The results of this study are illustrated in graphical form in FIGS. 10 and 11 and data is summarized in Table VI.

TABLE VI

|  | 15 min | 30 min | 45 min | 60 min | 75 min | 90 min |
|---|---|---|---|---|---|---|
| (1) Sarcosine alone | 0.496 | 0.405 | 0.974 | 1.423 | 2.102 | 1.801 |
| (2) Sarcosine + TSC | 0.512 | 2.963 | 6.058 | 7.949 | 10.208 | 11.629 |
| (3) Sarcosine + L-Leucine | 0.782 | 1.576 | 2.432 | 3.337 | 3.492 | 4.150 |
| (4) Sarcosine + L-Leucine + TSC | — | 1.304 | 5.754 | 8.032 | 10.174 | 11.246 |
| (1) Sarcosine + L-Leucine | 0.341 | 0.851 | 1.424 | 2.222 | 2.538 | 3.081 |
| (2) Sarcosine + L-Leucine + TSC | 0.297 | 0.701 | 1.127 | 1.875 | 2.205 | 2.734 |

L-Leucine permeability was enhanced in the presence of TSC, though the effect seems muted in the presence of sarcosine. Sarcosine permeability was also enhanced in the presence of TSC.

Example VII

Figure 12:
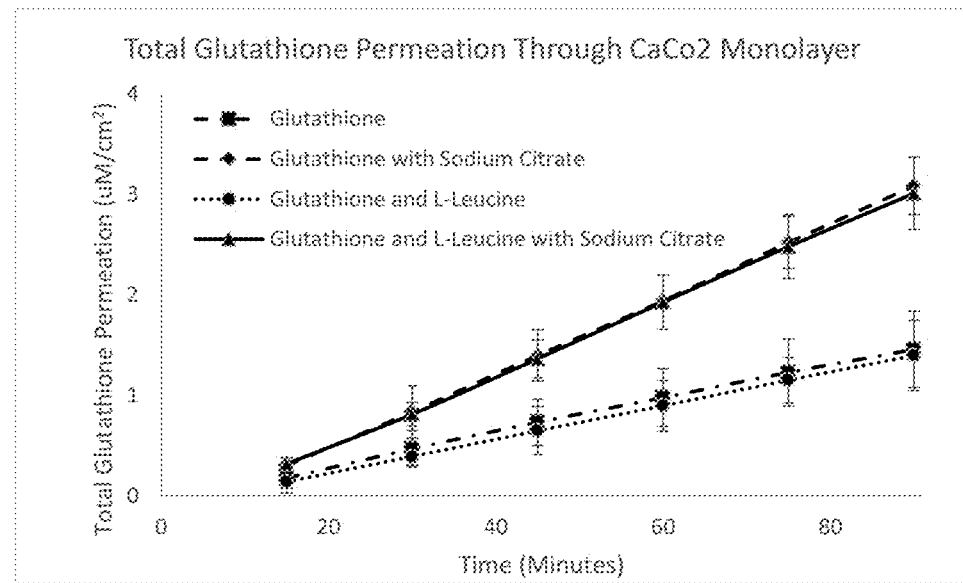
FIG. 12 is a graph comparing glutathione diffusion across a Caco2 barrier from solutions of (1) L-glutathione, (2) L-glutathione+TSC, (3) L-leucine+L-glutathione, and (4) L-leucine+L-glutathione+TSC, wherein $\mu M/cm^2$ are plotted for samples taken at 15 minute intervals over a 90 minute test.
Figure 13:
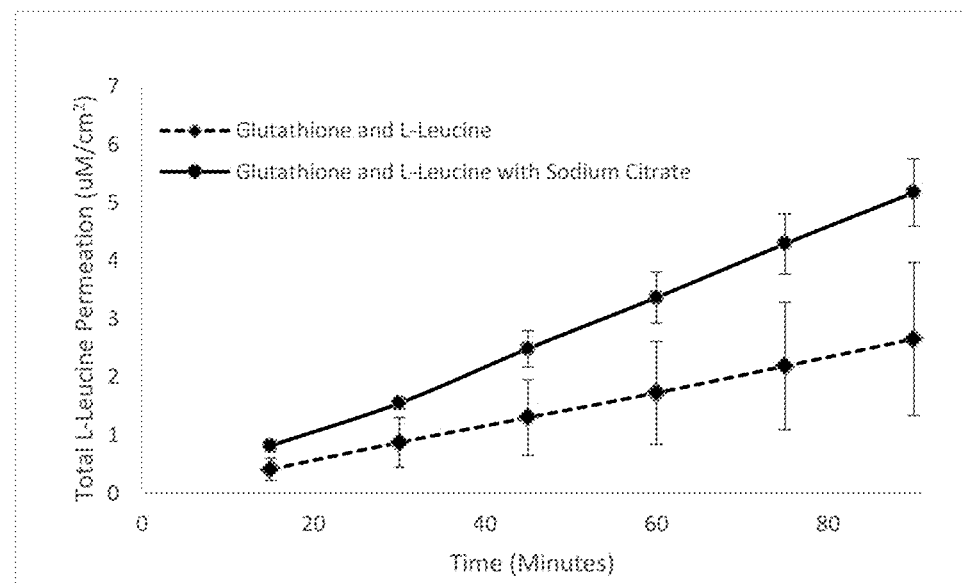
FIG. 13 is a graph comparing leucine diffusion across a Caco2 barrier from solutions of (1) L-leucine+L-glutathione, and (2) L-leucine+L-glutathione+TSC, wherein $\mu M/cm^2$ are plotted for samples taken at 15 minute intervals over a 90 minute test.

The permeability of the branched-chain amino acids Glutathione and L-Leucine through a Caco2 monolayer alone or in combination in the presence and absence of TSC was also tested. Again, undyed isotonic DPBS as receiver and donor buffer rather than HBSS was used due to interference with HBSS components in the HPLC. Three mL of 10 mM Glutathione or 10 mM Glutathione and 10 mM L-Leucine in DPBS alone or with 10 mM TSC was added to the donor chamber of each of 3 side by side diffusion cells with a confluent Caco2 Monolayer between (TEER~900 Ohm*cm2). Samples were taken at 15 minute intervals for 90 minutes and replaced with fresh isotonic DPBS. Samples were taken from donor chamber at time 0 and at 90 minutes. The previously seen peak in the receiver side samples which had not interfered with previous samples eluted at the same time as the Glutathione. To retrieve results this peak was averaged from time points in previous studies therefore these results represent an estimation by subtraction. Below are the results of these studies in Table VII below and illustrated in graph form in FIGS. 12 and 13.

TABLE VII

|  | 15 min | 30 min | 45 min | 60 min | 75 min | 90 min |
|---|---|---|---|---|---|---|
| (1) Glutathione alone | 0.177 | 0.467 | 0.731 | 0.977 | 1.227 | 1.456 |
| (2) Glutathione + TSC | 0.301 | 0.835 | 1.396 | 1.940 | 2.519 | 3.082 |
| (3) Glutathione w/L-Leucine | 0.139 | 0.391 | 0.647 | 0.895 | 1.151 | 1.394 |
| (4) Glutathione w/L-Leucine + TSC | 0.318 | 0.811 | 1.363 | 1.926 | 2.479 | 3.009 |
| (1) Glutathione w/L-Leucine | 0.404 | 0.866 | 1.293 | 1.722 | 2.180 | 2.658 |
| (2) Glutathione w/L-Leucine + TSC | 0.810 | 1.542 | 2.480 | 3.361 | 4.285 | 5.1688 |

Glutathione permeation was seen to be significantly increased in the presence of trisodium citrate. Leucine had no noticeable effect on the permeability of glutathione. As previously observed the permeability of Leucine was enhanced in the presence of trisodium citrate.

Example VIII

Figure 14:
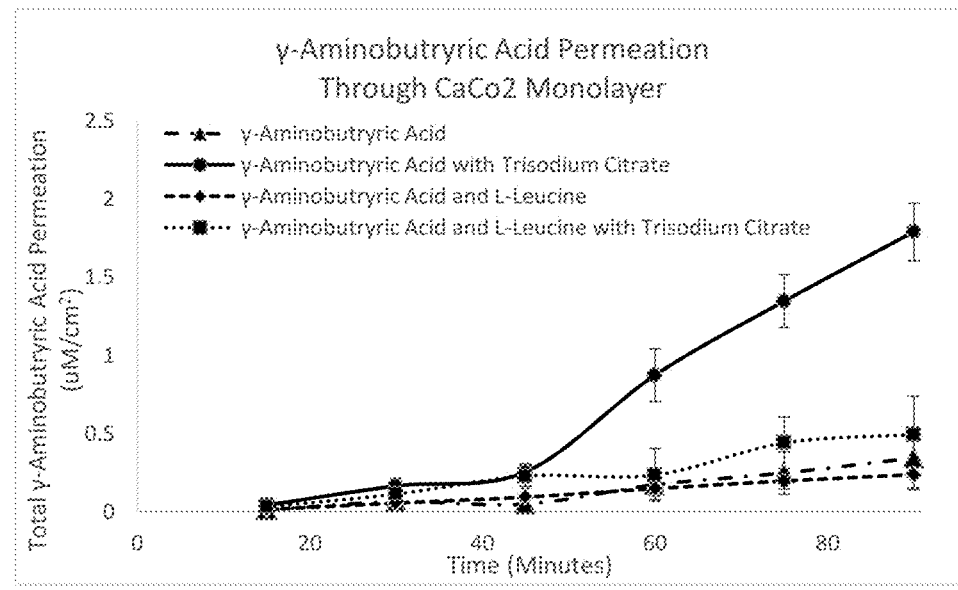
FIG. 14 is a graph comparing gamma-am inobutryic acid (GABA) diffusion across a Caco2 barrier from solutions of (1) GABA, (2) GABA+TSC, (3) L-leucine+GABA, and (4) L-leucine+GABA+TSC, wherein $\mu M/cm^2$ are plotted for samples taken at 15 minute intervals over a 90 minute test.
Figure 15:
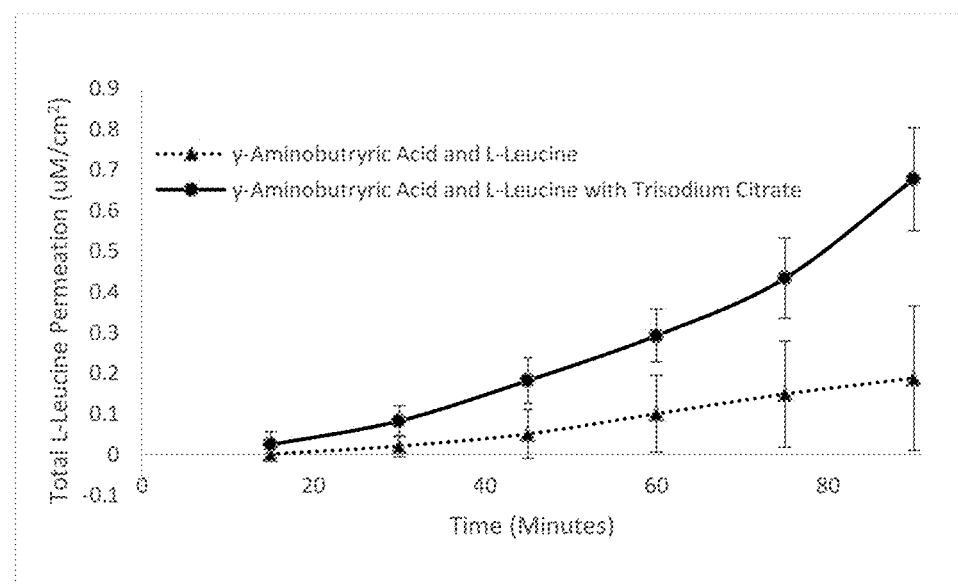
FIG. 15 is a graph comparing leucine diffusion across a Caco2 barrier from solutions of (1) L-leucine+GABA, and (2) L-leucine+GABA+TSC, wherein $\mu M/cm^2$ are plotted for samples taken at 15 minute intervals over a 90 minute test.

The permeability of gamma-am inobutryric acid (GABA) and L-Leucine through a Caco2 monolayer alone or in combination in the presence and absence of trisodium citrate ("TSC") was then tested. As before, for these experiments we used undyed isotonic DPBS as receiver and donor buffer rather than HBSS due to interference with HBSS components in the HPLC. In brief, 3 mL 10 mM GABA or 10 mM GABA and 10 mM l-leucine in DPBS alone or with 10 mM TSC was added to the donor chamber of each of 3 side by side diffusion cells with a confluent Caco2 monolayer between (TEER~900 Ohm*cm2). Samples were taken at 15 minute intervals for 90 minutes and replaced with fresh isotonic DPBS. Samples were taken from donor chamber at time 0 and at 90 minutes. Due to matrix interference and low concentrations GABA was not detectable by HPLC in receiver chamber samples. To retrieve results developed an LC/MS method and ran receiver chamber samples. The results of these studies are summarized below in Table VIII and illustrated graphically in FIGS. 14 and 15.

TABLE VIII

|  | 15 min | 30 min | 45 min | 60 min | 75 min | 90 min |
|---|---|---|---|---|---|---|
| (1) GABA alone | 0.013 | 0.065 | 0.051 | 0.174 | 0.249 | 0.346 |
| (2) GABA + TSC | 0.044 | 0.166 | 0.257 | 0.874 | 1.347 | 1.790 |
| (3) GABA + L-Leucine | 0.016 | 0.057 | 0.095 | 0.149 | 0.198 | 0.239 |
| (4) GABA + L-Leucine + TSC | 0.033 | 0.115 | 0.230 | 0.236 | 0.442 | 0.495 |
| (1) GABA + L-Leucine | — | 0.020 | 0.050 | 0.099 | 0.148 | 0.187 |
| (2) GABA + L-Leucine + TSC | 0.023 | 0.081 | 0.181 | 0.291 | 0.432 | 0.676 |

When used alone GABA permeation was seen to be significantly increased in the presence of TSC. In the presence of I-leucine with and without TSC the permeability of GABA was not significantly different as compared GABA alone. As previously observed the permeability of leucine was enhanced in the presence of TSC.

Example IX

Figure 16:
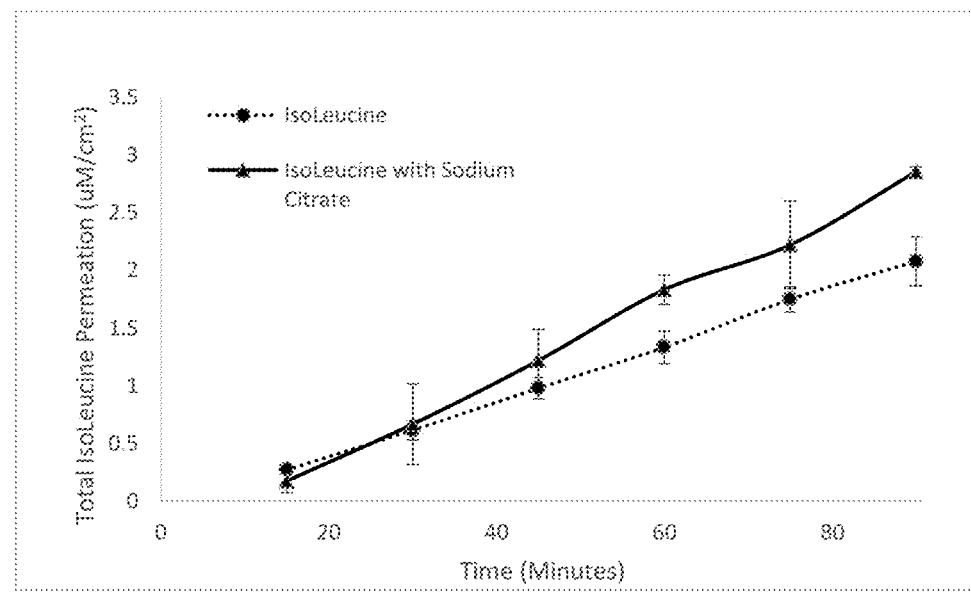
FIG. 16 is a graph comparing iso-leucine diffusion across a Caco2 barrier from formulations of (1) iso-leucine, and (2) iso-leucine+TSC, wherein $\mu M/cm^2$ are plotted for samples taken at 15 minute intervals over a 90 minute test.

The permeability of iso-leucine a Caco2 monolayer alone or in combination in the presence and absence of trisodium citrate ("TSC") was then tested. Undyed isotonic DPBS was used as receiver and donor buffer rather than HBSS due to interference with HBSS components and Valine in the HPLC. In brief 3 mM 10 mM Isoleucine or Valine in DPBS alone or with 10 mM trisodium citrate was added to the donor chamber of each of 3 side by side diffusion cells with a confluent Caco 2 Monolayer between (TEER~900 Ohm*cm2). Samples were taken at 15 minute intervals for 90 minutes and replaced with fresh isotonic DPBS. Below are the results of this study in table form, which are graphically illustrated in FIG. 16.

TABLE IX

|  | 15 min | 30 min | 45 min | 60 min | 75 min | 90 min |
|---|---|---|---|---|---|---|
| (1) Iso-leucine alone | 0.271 | 0.614 | 0.978 | 1.333 | 1.748 | 2.078 |
| (2) Iso-leucine + TSC | 0.174 | 0.666 | 1.218 | 1.831 | 2.220 | 2.853 |

Iso-leucine exhibited a substantially similar permeability shift and overall permeability increase to that exhibited by leucine as a result of the addition of trisodium citrate.

Example X

Figure 17:
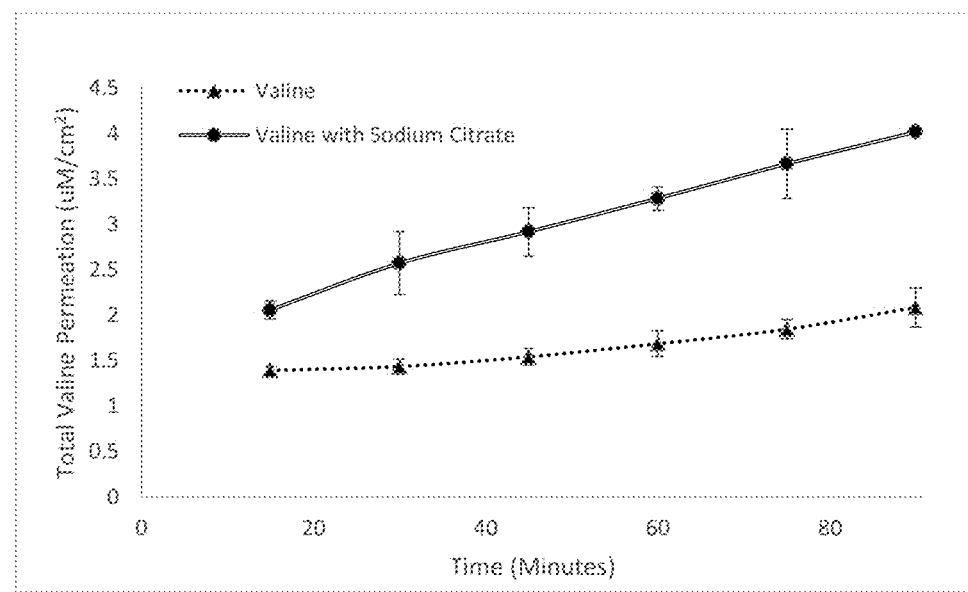
FIG. 17 is a graph comparing valine diffusion across a Caco2 barrier from solutions of (1) valine, and (2) valine+TSC, wherein $\mu M/cm^2$ are plotted for samples taken at 15 minute intervals over a 90 minute test.

The permeability of valine across a Caco2 monolayer alone or in combination in the presence and absence of TSC was then tested. Undyed isotonic DPBS was used as receiver and donor buffer rather than HBSS due to interference with HBSS components and Valine in the HPLC. In brief 3 mM 10 mM Valine in DPBS alone or with 10 mM trisodium citrate was added to the donor chamber of each of 3 side by side diffusion cells with a confluent Caco 2 Monolayer between (TEER~900 Ohm*cm2). Samples were taken at 15 minute intervals for 90 minutes and replaced with fresh isotonic DPBS. Data is summarized below in Table X and graphically illustrated in FIG. 17.

TABLE X

|  | 15 min | 30 min | 45 min | 60 min | 75 min | 90 min |
|---|---|---|---|---|---|---|
| (1) Valine alone | 1.388 | 1.431 | 1.537 | 1.682 | 1.841 | 2.081 |
| (2) Valine + TSC | 2.054 | 2.568 | 2.914 | 3.281 | 3.662 | 4.012 |

Valine exhibited a significantly greater permeability shift and overall higher permeability in the presence of trisodium citrate as compared to the shift and permeability seen with iso-leucine and leucine.

Example XI

In order to determine if further enhanced uptake was possible, formulations similar to those previously tested were enhanced by the addition of a commercially available polymer mixture called EUDRAGUARD® protect, which contains methacrylate copolymers. It is commercially described as "a highly robust and versatile polymer designed for immediate release formulations. It offers reliable taste and odor masking to ensure the product appeals to customers and protects ingredients from light, moisture and oxygen, which could impact ingredient effectiveness. Eudraguard coatings give a smooth and even finish, improving visual appeal and making the finished product easier to swallow. They also enhance storage stability." It is available under the product name EUDRAGUARD® protect and is described as "a ready-to-use powder that contains all the ingredients needed to form effective protective coatings for nutraceuticals. The spray suspension is formed by simply adding water to the ReadyMix while stirring." Exemplary methacrylate copolymers like those believed to be in EUDRAGUARD® protect include neutral methacrylate copolymers (e.g., poly(butylmethacrylate-co-(2-dimethylaminoethyl)-methacrylate-co-methylmethacrylate CAS No. 24938-16-7), anionic methacrylate copolymer (e.g., poly(methyl acrylate-co-methylmethacrylate-co-methacrylic acid CAS No. 26936-24-3), and/or basic methacrylate copolymer (e.g., poly(butyl methacrylate-co-(2-dimethylaminoethyl) methacrylate-co-methylmethacrylate, CAS No. 24938-16-17). In one embodiment, the weight percent of the methyl methacrylate copolymers mixed (rather than coated) with the supplements of the present invention constitutes 1-10%, more preferably 2-6% and most preferably 4-5%. Formulations were also further enhanced with cyclodextrin (available in α, β, and γ forms and in mixtures thereof) and polyethylene glycols (PEGs) optimally PEG 3350.

Thereafter, a set of formulation diffusion studies were undertaken using a Caco2 cellular model again similar to that described in the publication by A. K. Dash, et al., "Evaluation of Creatine Transport Using Caco-2 Monolayers as an In Vitro Model for Intestinal Absorption". Four formulations were studied:
(1) a multi-component formulation/mixture of creatine monohydrate:leucine:Eudraguard protect: α-cyclodextrin:PEG 3350 by mass (65:20:5:5:5);
(2) formulation (1) in 10 mM trisodium citrate ("TSC");
(3) a "raw drug" 2-component creatine monohydrate: leucine (75:25 percent by mass); and
(4) "raw drug" 2-component creatine monohydrate:leucine in a 10 mM TSC.

For all samples 10 Mm creatine was present in the initial solution. Samples from each formulation were monitored apical to basolateral for 90 minutes in 15 minute increments through a Caco-2-membrane registering an average TEER of 2500 Ohm*cm2. Samples were monitored for creatine, leucine and creatinine content. No significant quantities of creatinine were detected during the study.

Once again, the tests were undertaken using a Caco-2 cells so as to more closely approximate transport of creatine and branched-chain amino acids across mucosal cell membranes in vivo than might be reflected in other utilizing non-human cell sources or non-mucosal cell types. In the permeation tests illustrated herein, simulated gastric and intestinal buffers 0.2N NaOH was used, with 1 g NaOH diluted as needed with 125 mL deionized water. To simulate intestinal fluid without enzymes, 6.8 g monobasic potassium phosphate was mixed in 77 mL of 0.2 N sodium hydroxide, and pH adjusted to 6.8±0.1 using NaOH or HCl, as needed. Thereafter the solution was diluted with 1 L deionized water to achieve a final pH of preferably 6.8±0.1 To simulate gastric fluid without enzymes, 2.0 g sodium chloride was added to 7.0 mL concentrated HCl, and the solution diluted to 1 liter. The pH was approximately 1.2.

Figure 18:
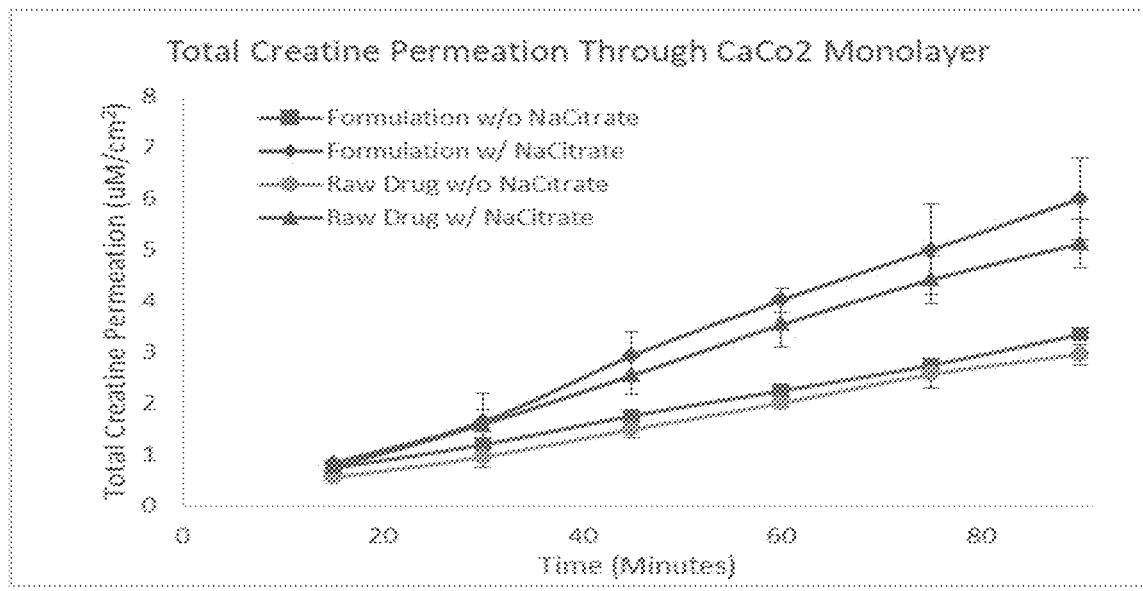
FIG. 18 is a graph comparing creatine diffusion across a Caco2 barrier for raw drug formulations of leucine+creatine monohydrate with and without TSC, with formulations also containing Eudraguard protect, α-cyclodextrin and PEG (with and without TSC) wherein $\mu M/cm^2$ are plotted for samples taken at 15 minute intervals over a 90 minute test.

Creatine permeation through the Caco-2 monolayer is illustrated in the FIG. 18 graph—the creatine monohydrate/leucine formulation tested in the absence of TSC as measured at 30, 45, 60, 75 and 90 minutes after test start, showed relatively poor permeation for creatine and was substantially similar to creatine permeation measured for Formulation (1) also without TSC present—measuring approximately 2.95 mM/cm2 of permeation at 90 minutes. Raw Drug (4)—the creatine monohydrate/leucine formulation in the TSC solution measured only slightly more, approximately 5.00 mM/cm2 of permeation at 90 minutes. Permeation for the complete Formulation (2) in the TSC solution was at all measuring points superior, and at 90 minutes measured 5.99 mM/cm2 of creatine permeation.

Figure 19:
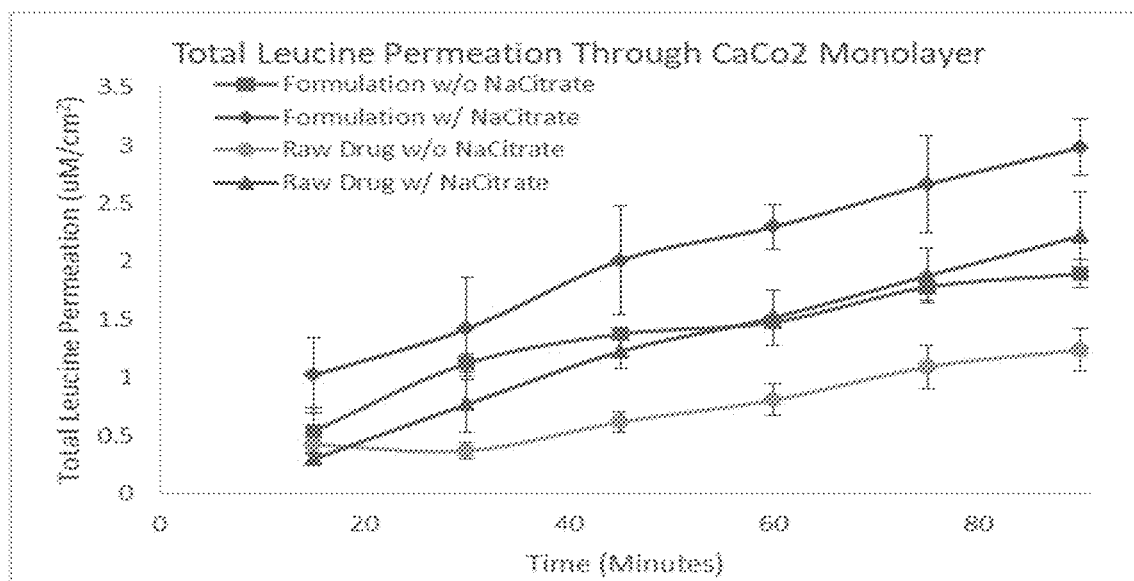
FIG. 19 is a graph comparing leucine diffusion across a Caco2 barrier for raw drug formulations of leucine+creatine monohydrate with and without TSC, with formulations also containing Eudraguard protect, α-cyclodextrin and PEG (with and without TSC) wherein $\mu M/cm2$ are plotted for samples taken at 15 minute intervals over a 90 minute test.

Leucine permeation was also measured, with the results graphically illustrated in FIG. 19. The 2-component creatine monohydrate/leucine formulation in the absence of TSC was measured for leucine permeation at 30, 45, 60, 75 and 90 minutes after test start, and showed consistently less permeation than Formulation 2, the complete formulation without any TSC solution present which measured approximately 1.89 mM/cm2 of leucine permeation at 90 minutes. At 90 minutes after test start, Formulation (1)—the multi-component creatine monohydrate/leucine formulation in the TSC solution measured slightly more, 2.22 mM/cm2 of leucine permeation at 90 minutes. Permeation for Raw Drug (4) the 2-component (raw drug) formulation in the TSC solution measured more permeation throughout the test period, which at 90 minutes measured 2.22 mM/cm2 of leucine permeation. Permeation for the multi-component Formulation (2) in the TSC solution was at all measuring points superior, and at 90 minutes measured 2.98 mM/cm2 of leucine permeation. Data from all measurements are summarized below in Table IX.

TABLE IX

|  | 15 min | 30 min | 45 min | 60 min | 75 min | 90 min |
|---|---|---|---|---|---|---|
| (1) formulation only CREATINE: | 0.731 | 1.19 | 1.75 | 2.24 | 2.74 | 3.34 |
| (2) formulation w/TSC CREATINE: | 0.827 | 1.63 | 2.92 | 4.01 | 5.00 | 5.99 |
| (3) raw drug only CREATINE: | 0.544 | 0.945 | 1.49 | 2.00 | 2.56 | 2.95 |
| (4) raw drug w/TSC CREATINE: | 0.739 | 1.58 | 2.53 | 3.53 | 4.41 | 5.12 |

TABLE IX-continued

|  | 15 min | 30 min | 45 min | 60 min | 75 min | 90 min |
|---|---|---|---|---|---|---|
| (1) formulation only LEUCINE: | 0.423 | 1.12 | 1.37 | 1.48 | 1.78 | 1.89 |
| (2) formulation + TSC LEUCINE: | 1.02 | 1.42 | 2.01 | 2.30 | 2.66 | 2.98 |
| (3) raw drug only LEUCINE: | 0.423 | 0.368 | 0.617 | 0.805 | 1.09 | 1.24 |
| (4) raw drug + TSC LEUCINE: | 0.298 | 0.770 | 1.22 | 1.52 | 1.88 | 2.22 |

It is readily observed from this study that the presence of trisodium citrate contributes substantially to increased permeation of both creatine and leucine across the Caco-2 cells. It is believed that these results are both synergistic with respect to creatine and leucine transport when both constituents are in a single formulation, that these synergistic results would also be applicable to compositions consisting of creatine monohydrate and one or more branched-chain amino acids selected from the group consisting of leucine, iso-leucine and valine.

In order to maximize the synergistic effect of substantially increased creatine and branched-chain amino acid uptake across digestive tract mucosa (including esophageal, stomach and intestinal mucosa), the ratio molar proportions of sodium in the trisodium citrate to the branched-chain amino acid(s) (and optionally creatine) must be substantial. The most preferred formulation includes leucine and/or other branched-chain amino acid with trisodium citrate, as such a formulation provides a substantial and sufficient quantity of sodium to optimize transport and absorption of the one or more branched-chain amino acid(s) such that a synergistic relationship is believed to result, and thereby enhancing the transport of the amino acid(s) to an extent not seen when other salts alone (such as when sodium chloride or sodium ascorbate is used). Most preferred formulations of leucine (and/or other branched-chain amino acids) to trisodium citrate results when the weight percent of the sodium in the trisodium citrate to the leucine (or to the total of all branched-chain amino acids) is at least 6% by weight. Acceptable ranges by weight of the sodium in the trisodium citrate to the one or more branched-chain amino acids are from 6% to 50%, 8% to 47%, 10% to 47%, and most preferably 25% to 47%.

Preferred daily dosing range of leucine (and/or other branched-chain amino acids) is from 1 to 10 grams, of trisodium citrate is from 500 mg to 5 grams, and, optionally, creatine monohydrate is from 1 to 8 grams. More preferred dosages of leucine and trisodium citrate are 1.5-4.5 grams and 0.75 to 2.5 grams, respectively. Most preferred dosages of leucine and trisodium citrate are 3 grams and 1.5 grams, respectively. If creatine monohydrate is also included in the composition to be ingested than an additional 1.5-4.5 grams of creatine monohydrate is preferred. Preferred daily dosing range of creatine when used alone with trisodium citrate is from 1 to 10 grams (more preferably 1 to 8 grams) and of the trisodium citrate is from 500 mg to 5 grams.

In terms of molar equivalents, most preferable dose formulations of leucine (and/or other branched-chain amino acid) to trisodium citrate are when the moles of leucine (or the total moles of all branched-chain amino acids) range from 0.0076 to 0.076 moles and the moles of trisodium citrate range from 0.0019 to 0.019 moles. If, at one end of this spectrum, a dose comprises 0.0076 moles of leucine and/or other branched chain amino acids and 0.0019 moles of trisodium citrate, the molar ratios may be reduced to 4:1. Since each mole of trisodium citrate comprises 3 moles of sodium, it can be seen that the most preferred ratio of the present invention of leucine and/or other branched-chain amino acids to sodium from trisodium citrate is 4:3. At the other end of the spectrum, if 0.076 moles of leucine and/or other branched chain amino acid are mixed with only 0.0019 moles of trisodium citrate, then it the molar ratio of the mixture if 0.004 to 0.0001 which can also be described as 40:1. Since there are 3 moles of sodium for each 1 mole of trisodium citrate, then the limit of an acceptable molar ratio of leucine and/or other branched-chain amino acid to sodium from any mixture of trisodium citrate is 40:3.

When creatine is included in the compositions of the present invention, most particularly when the preferred form of creatine—creatine monohydrate—is included in the formulations of the present invention which also include trisodium citrate, the most preferred molar ratio of creatine monohydrate:leucine:sodium wherein the sodium source is trisodium citrate, is 1:1:2. In this formulation, the percentage by weight of sodium to total weight of leucine (and/or other branched-chain amino acid) and creatine monohydrate is from 6% to 47%, more preferably 10% to 47%, most preferably 25% to 47%. However, it is expected that an enhanced transport effect will be present when the molar ratio of creatine monohydrate:leucine:sodium is from 1:1:0.5 to 1:1:3, or when percentages by weight of sodium are from approximately 6% to 47%.

Other preferred molar ratios of creatine monohydrate:leucine are from 1:5 to 5:1. This range includes molar ratios of creatine monohydrate:leucine of 2:3, 2:4, 3:2 and 4:2 and fractional values in between. Molar ratios of creatine monohydrate:leucine are acceptable in the range of from 1:10 to 10:1 (and include fractional molar ratios there between). In each of these cases, the weight of sodium compared to the weight of creatine monohydrate together with leucine preferably constitutes from about 6% to 47%, more preferably 8% to 33% and most preferably 8% to 20%.

Within the above listed preferable, more preferable and most preferable ratios by moles, daily dosage preferably is 2:1 leucine:trisodium citrate and 2:1:2 leucine:trisodium citrate:creatine monohydrate.

In alternate embodiments, the creatine monohydrate may be substituted in part or all with creatine hydrochloride. In alternate other embodiments, the creatine monohydrate may be substituted in part or all with creatine ethyl ester, creatine hydrochloride, creatine phosphate, creatine pyruvate, creatine ascorbate, creatine gluconate, creatine citrate, creatine nitrate, creatine magnesium chelate, and/or the salt forms of these listed creatines, provided that the uptake enhancements exhibited when creatine monohydrate is employed in combination with the sodium from the trisodium citrate are present.

Also, while leucine is the most preferred branched-chain amino acid for use in the formulations of the present invention, one or more branched-chain amino acids selected from the group consisting of leucine, valine and isoleucine may be substituted in all or part for the leucine component of the present invention.

In order to assess the uptake of leucine and creatine, in vivo, with and without enhancement with trisodium citrate, serum leucine concentrations enhanced of leucine ingested with trisodium citrate and/or creatine monohydrate may be compared to serum leucine concentrations of unenhanced leucine and creatine monohydrate. It is believed desirable to compare the effects on humans of 3 grams per day (in a single meal in the early evening) of creatine monohydrate to 3 grams per day of enhanced creatine (creatine monohydrate and leucine combined with trisodium citrate on serum creatine concentrations in human subjects will evidence measurable and significant differences. Preferable comparative doses to be ingested daily include: (1) enhanced leucine comprising 3 g leucine and 1.5 g sodium citrate; (2) standard leucine comprising 3 g leucine; (3) enhanced creatine monohydrate combined with sodium citrate containing 3 g creatine monohydrate and 1.5 g sodium citrate; (4) standard creatine monohydrate containing 3 grams without supplementation; and (5) enhanced creatine/leucine containing 3 g creatine monohydrate, 3 g leucine, and 1.5 g sodium citrate. In each case, the single dose is mixed with 8 fluid ounces of water and ingested. Serum levels of leucine and creatine are then taken on subsequent days.

The creatine formulations and other embodiments of the present invention are expected to have particular utility in weight training programs, in muscle building regimens, and in minimizing symptoms of Parkinson's disease and of muscle-wasting diseases 45 and conditions, including but not limited to polymyositis, cachexia due to metabolic disease, cachexia due to cancer, anorexia nervosa, myasthenia gravis and rhabdomyolysis. When the leucine and creatine formulations and other embodiments of the present invention are used it minimize symptoms of Parkinson's disease and of muscle-wasting diseases and conditions, a regimen of from 2 to 20 grams per day of the leucine and/or creatine is contemplated.

Preferred embodiments of the present invention may be best characterized as an oral branched-chain amino acid supplement comprising one or more branched-chain amino acids selected from the group consisting of leucine, valine and iso-leucine, optionally creatine monohydrate, and trisodium citrate. A dose of supplements such as these contain at least 3 grams total of the one or more branched-chain amino acids and the optional creatine monohydrate, and the weight percent of sodium in the trisodium citrate to the total weight of the total of the one or more branched-chain amino acids and the optional creatine monohydrate is from 0.25% to 19%. Alternatively, the weight percent of the sodium in the sodium citrate to the total weight of total of the one or more branched-chain amino acids and the optional creatine monohydrate is from 2% to 15%.

In other embodiments of the present invention, an oral supplement dose may comprise at least 2 grams of leucine and at least 1 gram of sodium citrate. Other embodiments may comprise comprises 20-80% weight percent of the leucine and 10-50% the sodium citrate. A most preferred embodiment comprises leucine and sodium citrate present in a weight ratio of 2:1. Alternatively, in certain embodiments of the present invention, the weight percent of the sodium in the sodium citrate to the total weight of the one or more branched-chain amino acids is from 2% to 10%. In such formulations, the formulation preferably weight 10% through 45% leucine, 10% through 45% creatine monohydrate and 5% through 30% trisodium citrate. Alternatively a formulation may comprise by weight 30% through 50% leucine, 30% through 50% creatine monohydrate and 10% through 25% trisodium citrate. In formulations of the present invention, leucine, creatine monohydrate and trisodium citrate may be present in a ratio of 2:2:1 by weight. Doses preferably comprise at least 3 grams of leucine, at least 3 grams of creatine monohydrate and at least 1.5 grams of TSC.

In any of the oral supplement formulations described herein, creatine (preferably creatine monohydrate) may constitute 1 gram or more of the supplement.

It is further contemplated that trisodium citrate will enhance transport across mucosal membranes and thus bioavailability of not just of leucine, iso-leucine, valine, arginine, sarcosine, glutathione, gamma-aminobutyric acid, and creatine but also of carnosine, glutathione, glucosamine, arginine, cysteine, glycine, glutamine, proline, tyrosine, phenylalanine, threonine, tryptophan, methionine, lysine, histidine, alanine, aspartic acid, asparagine, glutamic acid and serine. More generally, such transport and increased bioavailability resulting from supplementation with trisodium citrate is expected to have a similar effect of increased bioavailability on protein hydrolysates, including single amino acids, dipeptides, tripeptides, oligopeptides. Protein hydrolysates may be obtained from sources such as whey, soybeans and eggs.

Example XII

A human clinical trial to evaluate the absorption pharmacokinetics (PK) of oral dosing of leucine by itself and in combination with trisodium citrate in a cross-over design with eight healthy male volunteers was also undertaken. Another separate study group with eight healthy male volunteers in a three-way crossover design was also evaluate to evaluate the absorption pharmacokinetics of oral dosing of creatine by itself, in combination with trisodium citrate, and in combination with trisodium citrate and leucine. All formulations studied were evaluated via blood draws taken upon commencement of the study and immediately after dosing over time (at 0, 30, 60, 180, 360 and 540 minutes) to determine the absorption into circulation to assess uptake and overall concentration. Each volunteer was fed a turkey sandwich prior to 8 p.m. the evening before, and fasted the next day. Random, coded and blinded dosing was done with each component formulation (e.g., 3 grams active ingredient plus 1.5 grams of trisodium citrate) in a fruit punch flavor sachet added to 8 ounces of water. Blood draws for plasma analysis were collected (with duplicates) at T=0 min, 30 min, 60 min, 180 min, 360 min and 540 minutes. Standard analytical methodology by LC-MS-MS with nanogram-picogram sensitivity was used to determine plasma leucine and creatine levels. PK parameters were determined, including Cmax (active absorption uptake max concentration), Tmax (time to max concentration), T ½ (time to ½ of concentration clearance) and AUC (concentration area under the curve) were measured and calculated by established pharmacokinetic methods on all samples.

Statistical analysis of the resulting data by ANOVA (analysis of variance) and Paired student T-Test for significance plus other methods provided statistically significant findings for trisodium citrate+leucine, with Cmax and AUC that were statistically significant ($p<0.05$), and for trisodium citrate+creatine monohydrate, the C max was statistically significant ($p<0.05$). These data are consistent with the trisodium citrate having a significant role in the increasing the absorption of both creatine monohydrate as well as leucine. Unexpected and surprising in view of laboratory Caco2 studies interpreted as predicting the rise of creatine monohydrate with the presence of trisodium citrate and leucine would be superior to the combination of creatine monohydrate and trisodium citrate without leucine. Trisodium citrate is a very useful ingredient for efficient oral delivery in combination with either creatine monohydrate or leucine. Also, the trisodium citrate+creatine monohydrate+ leucine formulation was improved by 15-18% for Cmax for both creatine monohydrate and leucine, as well as AUC for leucine, but was not statistically significant. The data suggested that the addition of trisodium citrate can improve the absorption of the combination, although perhaps not to the degree of the individual paired components. Indeed, the addition of trisodium citrate to the oral formations improved the absorption uptake of both leucine and creatine monohydrate together, and significantly improved the overall concentration and circulating concentration (AUC) of leucine and significantly improved the overall uptake concentration of creatine monohydrate when combined separately with trisodium citrate. The results of this clinical study were both unexpected and surprising.

The invention claimed is:

1. An oral supplement comprising:
one or more bioactive components selected from the group consisting of leucine, iso-leucine, valine, arginine, sarcosine, glutathione, gamma-aminobutryric acid, and creatine; and
trisodium citrate,
wherein the weight ratio of the one or more bioactive components to sodium from the trisodium citrate is from 5:1 to 1:5, inclusive.

2. The oral supplement of claim 1, wherein the one or more bioactive components are selected from the group consisting of leucine, iso-leucine, valine and arginine.

3. The oral supplement of claim 2, wherein group of bioactive components further includes protein hydrolysates, dipeptides tripeptides, and oligopeptides.

4. The oral supplement of claim 1, the weight ratio of the one or more bioactive components to sodium from the trisodium citrate is from 2:1 to 1:2, inclusive.

5. The oral supplement of claim 4, wherein group of bioactive components further includes carnosine, glucosamine, cysteine, glycine, glutamine, proline, tyrosine, phenylalanine, threonine, tryptophan, methionine, lysine, histidine, alanine, aspartic acid, asparagine, glutamic acid and serine.

6. The oral supplement of claim 5, comprising at least 2 grams of leucine, at least 2 grams of creatine and at least 1.5 grams of trisodium citrate.

7. The oral supplement of claim 4, wherein group of bioactive components further includes protein hydrolysates, dipeptides, tripeptides, and oligopeptides.

8. The oral supplement of claim 1, wherein a dose of the oral supplement comprises at least 2 grams of leucine and at least 1 gram of trisodium citrate.

9. The oral supplement of claim 1, wherein the selected one or more bioactive components selected includes creatine and the creatine comprises at least 1 gram of the supplement.

10. The oral supplement of claim 9, wherein the one or more bioactive components is selected from the group consisting of leucine, iso-leucine and valine.

11. The oral supplement of claim 1, wherein the one or more bioactive components is selected from the group consisting of leucine, iso-leucine and valine.

12. The oral supplement of claim 1, wherein group of bioactive components further includes carnosine, glucosamine, cysteine, glycine, glutamine, proline, tyrosine, phenylalanine, threonine, tryptophan, methionine, lysine, histidine, alanine, aspartic acid, asparagine, glutamic acid and serine.

13. The oral supplement of claim 1, further comprising one or more forms of creatine selected from the group consisting of creatine monohydrate, creatine ethyl ester, creatine hydrochloride, creatine phosphate, creatine pyruvate, creatine ascorbate, creatine gluconate, creatine citrate, creatine nitrate, creatine magnesium chelate, the salt forms of these creatines.

14. The oral supplement of claim 13 wherein the one or more forms of creatine are selected from the group consisting of creatine monohydrate, creatine hydrochloride, creatine phosphate and salts thereof.

15. The oral supplement of claim 1, further comprising cyclodextrin selected from the group consisting of alpha-, beta- and gamma- cyclodextrins.

16. The oral supplement of claim 1, further comprising cyclodextrin and methacrylate copolymers.

17. The oral supplement of claim 1 further comprising cyclodextrin, methacrylate copolymers and polyethylene glycol.

18. (Originaled) The oral supplement of claim 17, wherein the combined weight percent of the cyclodextrin, methacrylate copolymers and polyethylene glycol comprise 2-20% of the weight percent of the supplement.

19. The oral supplement of claim 18, wherein the cyclodextrin, methacrylate polymers and polyethylene glycol each comprise 3-6 percent by weight of the supplement.

20. The oral supplement of claim 19, wherein the polyethylene glycol comprises PEG 3350.

21. The oral supplement of claim 19, wherein the polyethylene glycol comprises PEG 3350.

22. The oral supplement of claim 18, wherein the cyclodextrin, methacrylate polymers and polyethylene glycol each comprise 3-6 percent by weight of the supplement.

23. The oral supplement of claim 17, wherein the combined weight percent of the cyclodextrin, methacrylate copolymers and polyethylene glycol comprise 2-20% of the weight percent of the supplement.

24. The oral supplement of claim 1, wherein group of bioactive components further includes protein hydrolysates, dipeptides, tripeptides, and oligopeptides.

25. An oral supplement, comprising:
one or more bioactive components selected from the group consisting of leucine, iso-leucine, valine, arginine, sarcosine, glutathione, gamma-aminobutryric acid, and creatine; and
trisodium citrate,
wherein a dose of the supplement contains at least 2 grams total of the one or more bioactive components, and the weight ratio of the one or more bioactive components to sodium from the trisodium citrate is from 10:1 to 1:10, inclusive.

26. The oral supplement of claim 25, wherein the selected one or more bioactive components includes creatine and the creatine comprises at least 1 gram of the supplement.

27. The oral supplement of claim 25, wherein the one or more bioactive components is selected from the group consisting of leucine, iso-leucine and valine.

28. The oral supplement of claim 25, wherein group of bioactive components further includes carnosine, glucosamine, cysteine, glycine, glutamine, proline, tyrosine, phenylalanine, threonine, tryptophan, methionine, lysine, histidine, alanine, aspartic acid, asparagine, glutamic acid and serine.

29. The oral supplement of claim 28, further comprising cyclodextrin selected from the group consisting of alpha-, beta- and gamma- cyclodextrins.

30. The oral supplement of claim 28, further comprising cyclodextrin and methacrylate copolymers.

31. The oral supplement of claim 28 further comprising cyclodextrin, methacrylate copolymers and polyethylene glycol.

32. The oral supplement of claim 25, wherein group of bioactive components further includes protein hydrolysates, dipeptides, tripeptides, and oligopeptides.

33. The oral supplement of claim 25, wherein the one or more bioactive ingredients are selected from the group consisting of alanine, arginine and glutathione.

34. The oral supplement of claim 28 wherein bioactive components are selected from the group consisting of alanine, arginine and glutathione.

35. An oral supplement formulation by weight comprising 1-10 grams of a branched chain amino acid selected from the group consisting of leucine iso-leucine and valine, 1-10 grams of creatine monohydrate and 0.5-5 grams of trisodium citrate.

36. An oral formulation comprising leucine, creatine monohydrate and trisodium citrate having a sufficient concentration to enhance the uptake of the leucine and the creatine monohydrate,
wherein the weight ratio of the total of the leucine plus creatine from the creatine monohydrate to sodium from the trisodium citrate is from 5:1 to 1:5, inclusive.

* * * * *